(12) United States Patent
Kolko et al.

(10) Patent No.: US 10,456,522 B2
(45) Date of Patent: Oct. 29, 2019

(54) MONITORING DEVICE

(71) Applicant: Shift Labs, Inc., Seattle, WA (US)

(72) Inventors: Beth Elise Kolko, Seattle, WA (US);
Koji Intlekofer, Seattle, WA (US);
Michael Connolly, Seattle, WA (US)

(73) Assignee: Shift Labs, Inc., Seattle, WA (US)

( * ) Notice: Subject to any disclaimer, the term of this patent is extended or adjusted under 35 U.S.C. 154(b) by 0 days.

(21) Appl. No.: 16/389,554

(22) Filed: Apr. 19, 2019

(65) Prior Publication Data

US 2019/0247575 A1 Aug. 15, 2019

Related U.S. Application Data

(63) Continuation-in-part of application No. 15/487,335, filed on Apr. 13, 2017, now Pat. No. 10,265,468, and a continuation-in-part of application No. 15/362,646, filed on Nov. 28, 2016, now Pat. No. 9,962,488, which is a continuation of application No. 14/923,427, filed on Oct. 26, 2015, now Pat. No. 9,533,095, which is a continuation of application No. 14/188,669, filed on Feb. 24, 2014, now Pat. No. 9,199,036.

(60) Provisional application No. 62/323,051, filed on Apr. 15, 2016, provisional application No. 61/769,109, filed on Feb. 25, 2013.

(51) Int. Cl.
*A61M 5/168* (2006.01)
*G01F 1/58* (2006.01)

(52) U.S. Cl.
CPC ...... *A61M 5/1689* (2013.01); *A61M 5/16804* (2013.01); *G01F 1/58* (2013.01); *A61M 2205/3306* (2013.01); *A61M 2205/502* (2013.01)

(58) Field of Classification Search
CPC .................................. A61M 5/16; G01F 1/58
See application file for complete search history.

(56) References Cited

U.S. PATENT DOCUMENTS

| | | | | |
|---|---|---|---|---|
| 4,712,006 A | * | 12/1987 | Zemel | E21B 47/1015 250/256 |
| 8,545,759 B2 | * | 10/2013 | Niazi | G01N 21/8507 422/119 |
| 2012/0040331 A1 | * | 2/2012 | Niazi | G01N 21/8507 435/3 |
| 2013/0344584 A1 | * | 12/2013 | Niazi | G01N 21/8507 435/288.7 |

* cited by examiner

*Primary Examiner* — Jewel V Dowtin
(74) *Attorney, Agent, or Firm* — Lowe Graham Jones PLLC

(57) ABSTRACT

A monitoring device provided for monitoring the delivery of fluids through a drip chamber. The device includes an electromagnetic radiation (EMR) source and an EMR detector. The device includes a tubing set mount for receiving a flange or other portion of a tubing set, such that fluid falling through the drip chamber of the tubing set is detected by the detector.

15 Claims, 20 Drawing Sheets

MONITORING DEVICE

PRIORITY CLAIM

This application is a continuation-in-part of U.S. application Ser. No. 15/487,335, filed Apr. 13, 2017, which is a continuation-in-part of U.S. application Ser. No. 15/362,646, filed Nov. 28, 2016, which is a continuation of U.S. application Ser. No. 14/923,427, filed Oct. 26, 2015, now U.S. Pat. No. 9,533,095, which is a continuation of U.S. application Ser. No. 14/188,669, filed Feb. 24, 2014, now U.S. Pat. No. 9,199,036, which claims the benefit of U.S. provisional application No. 61/769,109, filed Feb. 25, 2013, and this application further claims the benefit of U.S. provisional application No. 62/323,051 filed Apr. 15, 2016, the contents of each of which are incorporated by reference.

FIELD OF THE INVENTION

The present disclosure relates generally to the delivery of intravenous fluids, more specifically to the monitoring of the delivery of fluids intravenously to a subject

BACKGROUND OF THE INVENTION

In a variety of settings, it may be useful to ensure precise delivery of intravenous fluids. One mode of intravenous fluid delivery is the gravity infusion set. One problem with using a gravity infusion set is the challenge of (a) establishing an accurate initial flow rate and (b) monitoring the flow rate over time.

A device for establishing and monitoring flow rate may be in the form of an all-in-one device having an infrared light source and photodiode, microprocessor, battery, and display. Such a device may also attach directly to the drip chamber and may provide continuous monitoring of a flow rate during a gravity infusion. An infrared light source and a photodiode may be mounted on opposing sides of the drip chamber so that the beam crosses through the path of a falling drip. The microprocessor may periodically measure the light sensed by the photodiode and, by sensing the change in detected light, can detect that a drop has fallen. By measuring the elapsed time between detected drops, the microprocessor can measure and then display a drop rate.

Two factors which contribute to successful monitoring of a gravity infusion via optical beam drop detection are (a) proper alignment of a sensing element on the drip chamber body and (b) secure attachment of a monitoring device to the drip chamber. If either of these factors are compromised, incomplete or inaccurate monitoring can result, as the beam may not be properly aligned to sense each falling drop, or the device might slip out of alignment. An all-in-one device may be subject to user misalignment on the drip chamber. In addition, design considerations for an all-in-one device may be complicated by aspects employed to securely attach the device to a wide variety of user-supplied drip chambers, which may vary significantly in geometry and materials of construction.

SUMMARY OF THE INVENTION

The present disclosure provides devices, methods, and systems for providing real time monitoring of a fluid flow rate and an accumulated total volume through a drip chamber.

Various embodiments of presently disclosed fluid flow rate monitoring devices include a source enabled to emit electromagnetic radiation (EMR), a detector enabled to generate a detector signal, a device body configured and arranged to position the source and the detector about at least one outer surface of the drip chamber such that the source and the detector define an optical path across the drip chamber, wherein fluid between the source and the detector inhibits EMR travelling along the optical path; a device body configured and arranged to position the source and the detector about at least one outer surface of the drip chamber such that the source and the detector define an optical path across the drip chamber, wherein fluid between the source and the detector inhibits EMR travelling along the optical path; and a processor device that executes instructions that perform actions. The actions include detecting a fluid drop based on at least a difference between a plurality of detector signal values temporally separated by a predetermined lag time and determining the flow rate of fluid based on at least a predetermined drip factor and detecting a plurality of fluid drops.

In some embodiments, detecting the fluid drop may be further based on a comparison of a plurality of temporally ordered difference values, wherein each of the plurality of difference values correspond to differences in the plurality of detector signals that are temporally separated by the lag time. Additionally, the actions may further include vetoing a detection of a second fluid drop when a temporal difference between the detection of the second fluid drop and a detection of a first fluid drop is less than a predetermined lockout time.

In at least one of the various embodiments, detecting the fluid drop may further include generating a drop waveform based on detector signal values sampled at a plurality of temporally ordered times, wherein the drop waveform is modulated by the fluid drop, generating a lag time difference waveform based on at least the lag time and a plurality of differences of the drop waveform corresponding to different times, and detecting the fluid drop based on at least a signal included in the lag time difference waveform.

In some embodiments, the source may be a light emitting diode (LED). In some embodiments, the detector may be a photodiode. In at least one of the various embodiments, the source may be further enabled to emit EMR within a wavelength window, wherein wavelengths within the wavelength window are longer than visible light wavelengths and a sensitivity of the detector is greater for at least a portion of the wavelengths within the wavelength window than for visible light wavelengths.

In some embodiments, the actions may further include detecting a first fluid drop at a first detection time, adding the first detection time to a drop history buffer, wherein the drop history buffer includes at least a plurality of other detection times and each of the other detection times corresponds to a previously detected fluid drop, removing at least one of the other detection times from the drop history buffer, determining an average drop rate based on at least the detection times included in the history buffer, and determining a drip stability based on a comparison of a plurality of temporal distances between the detection times included in the drop history buffer. In some embodiments, the device may include a battery. In some embodiments, power provided to at least one of the detector and the source is pulsed. The provided power may include a bias current. In at least one of the various embodiments, bias current provided to the detector and sources is pulsed at a predetermined frequency.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Figure 1A:
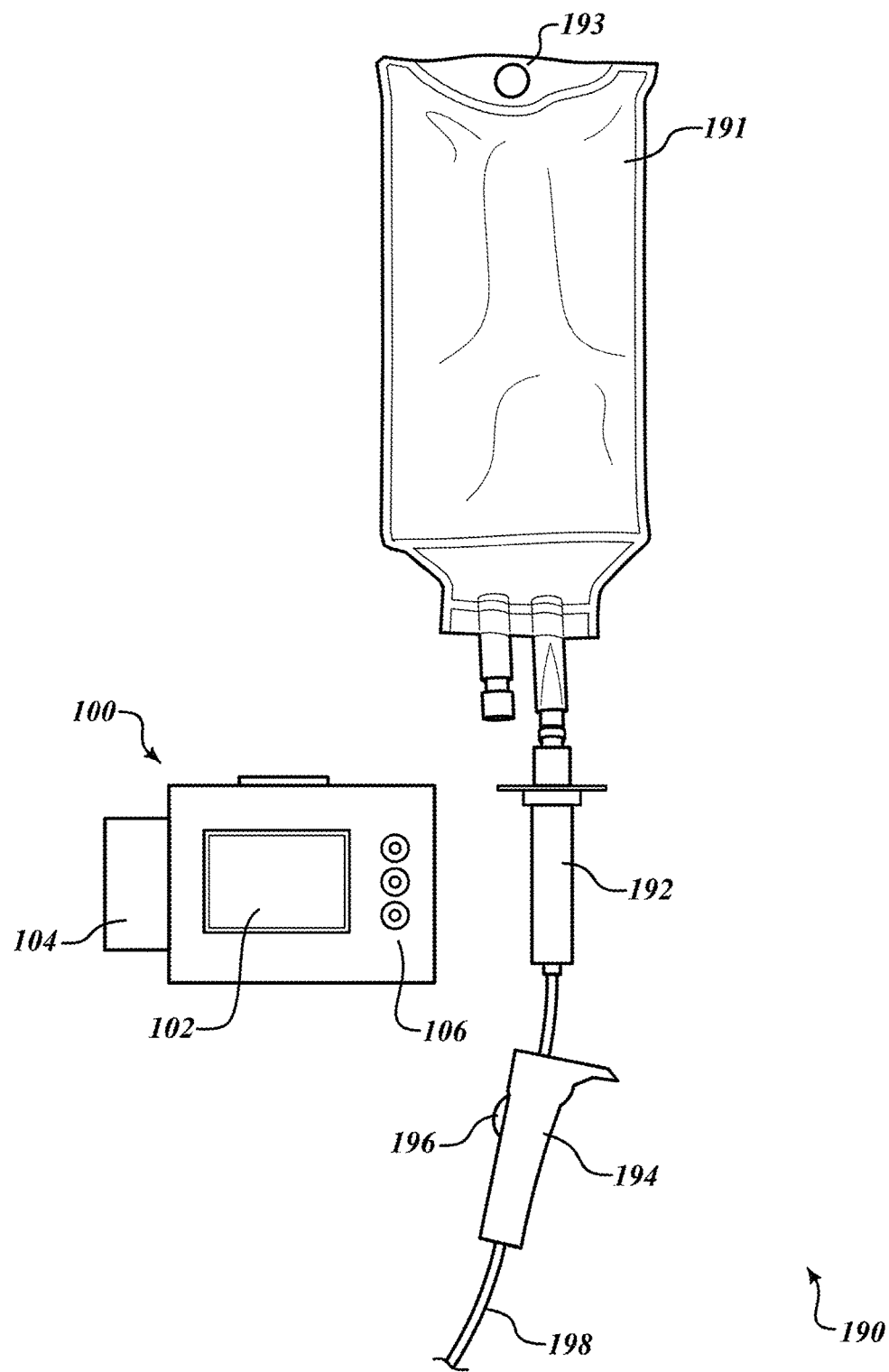
FIG. 1A shows a flow rate monitoring device adjacent to a gravity fed infusion set that includes a drip chamber according to embodiments of the present disclosure.

A preferred monitoring system may consist of a disposable gravity drip set containing drip sensing elements and a mechanical or electrical interface, and a monitoring unit which interfaces mechanically or electrically with this drip set. In this system, the monitoring unit may receive the sensor values and perform continuous or other monitoring of the infusion. This system may at least partially mitigate both the sensor alignment and secure attachment issues that may be seen with all-in-one infusion monitoring devices.

Terms defined herein have meanings as commonly understood by a person of ordinary skill in the areas relevant to the present disclosure. Terms such as "a," "an," and "the" are not intended to refer to only a singular entity, but include the general class of which a specific example may be used for illustration. The terminology herein is used to describe specific embodiments of the disclosure, but its usage does not delimit the disclosure, except as outlined in the claims.

As used herein, the term "electromagnetic radiation" (EMR) is not intended to be limiting. In contrast, as used throughout the present disclosure, EMR may refer to any form of energy relating to the propagation of electromagnetic waves and/or photons. The term EMR is not limited to a specified range of wavelengths or frequencies within the electromagnetic spectrum. Rather, EMR, as used herein may include radio waves, microwaves, infrared (IR) radiation, visible light, ultraviolet (UV) radiation, X-rays, gamma rays, or any other such wavelengths or frequencies of EMR.

As used herein, the terms "EMR source" and "source" are not intended to be limiting. In contrast, as used throughout the present disclosure, both "EMR source" and "source" may refer to any device enabled to emit EMR. Non-limiting examples of sources include light emitting diodes (LEDs), lasers, light bulbs, and the like.

As used herein, the terms "EMR detector" and "detector" are not intended to be limiting. In contrast, as used throughout the present disclosure, both "EMR detector" and "detector" may refer to any device enabled to generate a signal when in the presence of EMR. In some embodiments, the nature of the signal may be electrical, optical, mechanical, or a combination thereof. A generated electrical signal may be analog or digital in nature. Some detectors may be referred to as photodetectors or photosensors. Non-limiting examples of detectors include photodiodes, reverse-biased LEDS, active-pixel sensors (APS), avalanche-photodiode (APD), charge-coupled devices (CCD), photoresistors, photomultiplier tubes, photovoltaic cells, and the like.

As used herein, the term "processor device" is not intended to be limiting. Rather, as used throughout the present disclosure, processor device may refer to one or more devices enabled to execute instructions that perform actions. In some embodiments, a processor device may receive input and provide corresponding output in response to the received input. In some embodiments, processor device may include a programmable microcontroller. In some embodiments, a processor device may include a microprocessor. A processor device may include a field programmable gate array (FPGA). In other embodiments, a processor device may include an application specific integrated circuit (ASIC). In some embodiments, a processor device may include a computer and/or a mobile device. In some embodiments, a processor device may include a processing core, memory, input/output peripherals, logic gates, Analog-to-Digital Converters (ADCs) and such. In some embodiments, a processor device may include a plurality of processor devices in communication with one another across a network or a bus.

Briefly stated, various embodiments of the devices, methods, and systems included herein are directed towards, but not limited to monitoring the flow rate and total volumetric amount of a fluid, or accumulated fluid dose, delivered to a target through an infusion set, tubing set, or other mechanism. The target may be a medical patient and the fluids may be delivered intravenously.

A handheld monitoring device may be affixed to a drip chamber included in the infusion set. By employing an embedded EMR source and an embedded EMR detector, individual drops falling within the drip chamber may be detected and counted in real time. Furthermore, the time between each successive drop may be determined. By monitoring the rate of drops falling in the drip chamber and applying an appropriate drip factor, a fluid flow rate may be determined. Also, a total volumetric amount, or accumulated dose, of fluid delivered to the target may be determined.

The determined flow rate and total accumulated fluid dose may be provided in real time, to a user, through a user interface. The user interface may include a display unit, input buttons or an alpha-numeric keypad, and an audible speaker. In some embodiments, the user input and output functions may be enabled through a touch-sensitive display device.

The user may provide various input information, such as the drip factor, the target fluid flow rate, the target total dose, target flow stability, and the like, through the user interface. The user may also provide corresponding tolerances and/or ranges associated with these target parameters through the user interface.

If the flow becomes unstable, the monitored flow rate falls outside of a tolerance range, a total volumetric dose has been achieved or surpassed, or if the flow ceases, the device may provide various alerts to a user. These alerts may include audio alerts provided by the speaker. The alerts may also include visual alerts provided by the display device. In some embodiments, at least some of the alerts may be provided in real time to remote devices, including but not limited to servers/clients, mobile devices, desktop computers, and the like.

Furthermore, the handheld device may be attached or affixed to the drip chamber with a spring-loaded clip. In other embodiments, a trench or a channel included in the monitoring device may enable "snapping" the device onto the clip chamber. The device may be battery operated or power may be supplied through an external source, such as a wall socket. Some embodiments may include a backup battery. In at least one of the various embodiments, power may be supplied to a monitoring device by employing a solar-powered battery.

In some embodiments, the device may be networked to remote devices, such as a remote computer, a smart phone, or a tablet. Through network means, the device may provide real time information to such remote devices. A remote user may operate the user interface remotely. In some embodiments, the device may be operated and monitored through an application, such as an app running on a mobile device.

Furthermore, the device may be enabled to generate log files including the monitored flow rates, corresponding stabilities, and total delivered fluid dosages. The log files may also include other operational parameters, such as user provided inputs. These log files may be included in a patient's medical history files. In some embodiments, a remote networked computer may monitor the device and generate the log files. The log files may be provided to and archived by other systems, such as cloud-based storage systems.

Although many embodiments included herein are discussed in the context of delivering fluids through an infusion set, it should be understood that the present invention is not so limited. The present invention may be used in any context where fluids are being transported in the form of individual drops, for at least a portion of the total distance that the fluid is being transported. For instance, the present invention may be employed in any context where fluids drops are detectable. Examples include, but are not limited to fluid flowing through a drip chamber, a nozzle, a valve, an aperture, or the like. Such contexts include, but are not limited to industrial uses, governmental/academic/industrial research, and the like.

FIG. 1A shows an embodiment of flow rate monitoring device 100 adjacent to infusion set 190. In some embodiments, infusion set 190 may be a gravity fed infusion set, although the present invention is not so constrained. For instance, other means of inducing drop flow through a pathway, such as a pump, may be employed in various embodiments. In at least one of the various embodiments, flow rate monitoring device 100 may be a handheld device. Flow rate monitoring device 100 includes display unit 102. Display unit 102 may provide a user with real time data based on at least the monitored flow of fluid through infusion set 190. Although not shown in FIG. 1A, some embodiments may also include an audio interface, such as an audio speaker. An audio interface may provide the user with audio information, such as an audible alert when the monitored flow rate is outside of a specified range.

Monitoring device 100 includes user input interface 106. User input interface 106 may enable a user to provide inputs to the device such as, but not limited to, target flow rate, tolerance ranges, drip factors, lag times, lockout times, stability ranges, alarming functionality, display units, fluid types and the like. In some embodiments, input interface 106 may include buttons, alpha-numeric keypads, and the like. In some embodiments, input interface 106 may be integrated with display unit 102 by employing a touch sensitive display unit. Although not shown, in at least some embodiments, monitoring device 100 may include an audio input device, such as a microphone. Some embodiments may include voice recognition software so that a user may provide inputs through the audio input device. Monitoring device 100 includes coupler 104. Coupler 104 enables affixing or attaching monitoring device 100 to infusion set 190.

Infusion set 190 includes fluid source 191. Fluid source 191 may be an IV bag. Infusion set 190 may include a suspension means 193, such as a loop or hook attached to fluid source 191. Infusion set 190 may be suspended in a gravity field by employing suspension means 193. The suspension of infusion set 190 allows gravity to induce fluid flow through infusion set 190. When affixed to fusion set 190, monitoring device 100 may be suspended along with infusion set 190. In at least one of the various embodiments, coupler 104 may include a clip.

Infusion set 190 may include drip chamber 192. Due to gravity, fluid from fluid source 191 flows through drip chamber 192. Also, infusion set 190 may be enabled so that as long as the flow rate through infusion set 190 is below a critical threshold, the fluid flowing through drip chamber 192 is in the form of individual fluid drops. If the fluid flow rate is above the critical threshold, fluid flowing through drip chamber may become a continuous stream of fluid.

Some elements of infusion set 190 may be characterized by a drip factor. Drip factors depend upon physical characteristics of specific elements of infusion set 190, such as drip chamber 192 and tubing components such as fluid output 198, and combinations thereof. Drip factors correspond to the volume of fluid in each individual fluid drop that flows through a drip chamber of the specific infusion set. Drip factors may be expressed in units of gtt/mL, or drops per milliliter (mL) of fluid. For instance, for 1 mL of fluid to flow through an infusion set with a drip factor of 10 gtt/mL, 10 individual drops of fluid must flow through the drip chamber. Exemplary, but non-limiting, drip factor values corresponding to the combination of the various elements of infusion set 190 may include 10, 15, 20, and 60 gtt/mL. Throughout the present disclosure, references to an infusion set's drip factor may refer to the value of the drip factor corresponding to the combination of the various infusion set elements that a drip factor depends upon.

In some embodiments, drip factors may be expressed in alternative units, such as mL/gtt. In other embodiments, the drip factor may be expressed in drops per unit mass or weight if the density of fluid is known. Drip factors may also be expressed in mass or weight per drop. It is understood that the present disclosure is not limited to such example drip factors, and may accommodate any other appropriate values, units, or alternative ways to express or measure drip factors.

A flow rate of drops through drip chamber 192 may be converted to a fluid flow rate and vice versa based on the drip factor corresponding to infusion set 190. Additionally, a total number of drops, or accumulated flow of fluid may be determined by integrating or determining a sum of the flow rate of drops or fluid flow rate respectively, over successive points in time.

Infusion set 190 includes user handle 194 and roller clamp 196. By varying the position of roller clamp 196 along an edge of user handle 194, the combination of user handle 194 and roller clamp 196 enables a user to control the flow rate of individual fluid drops through drip chamber 192, and thus the flow rate of fluid through infusion set 190. Infusion set 190 includes fluid output 198. Fluid output 198 delivers fluid, originating at fluid source 191, to the intended target, and at the flow rate corresponding to the position of roller clamp 196.

Figure 1B:
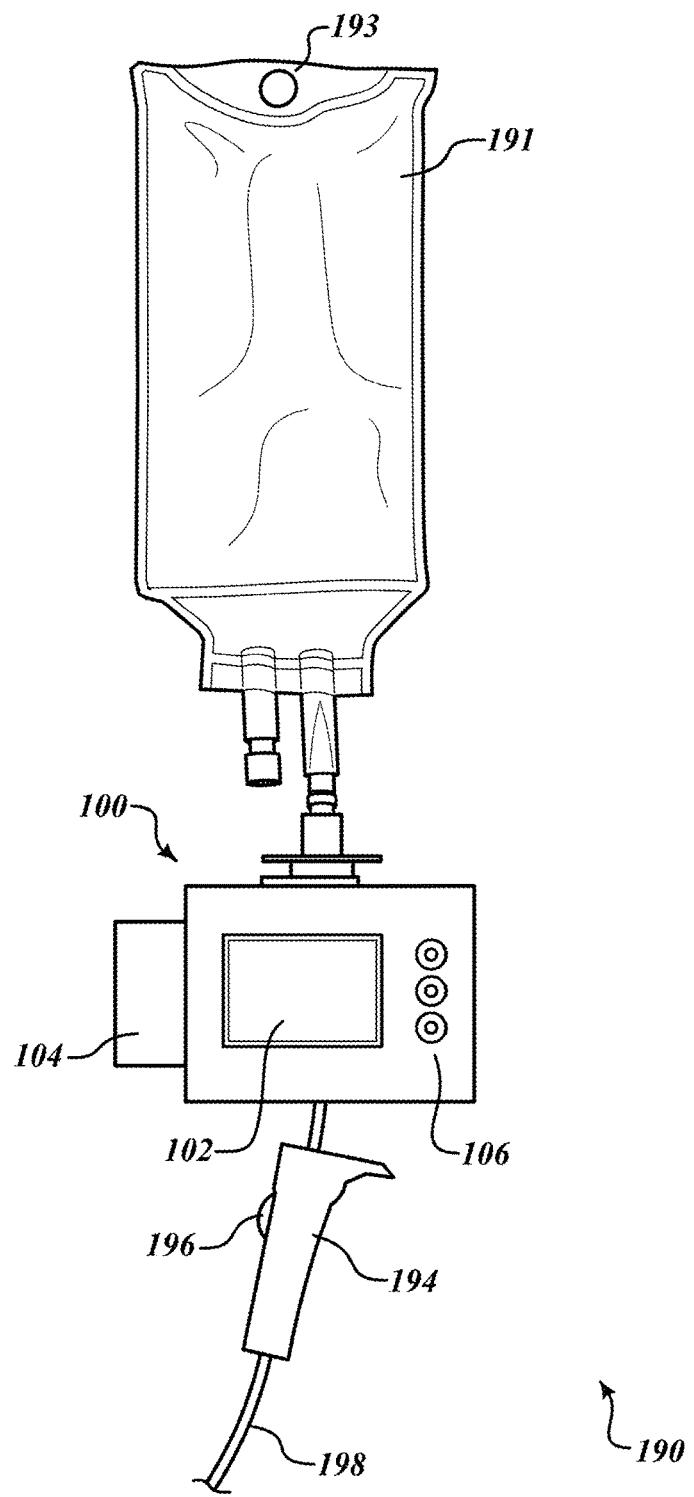
FIG. 1B shows a flow rate monitoring device affixed to a drip chamber included in a gravity fed infusion set according to embodiments of the present disclosure.

FIG. 1B shows flow rate monitoring device 100 attached to infusion set 190 by employing coupler 104. In some embodiments, monitoring device 100 may be attached to infusion set 190 by attaching or affixing monitoring device 100 to the drip chamber, which is hidden from view by monitoring device 100.

Figure 8A:
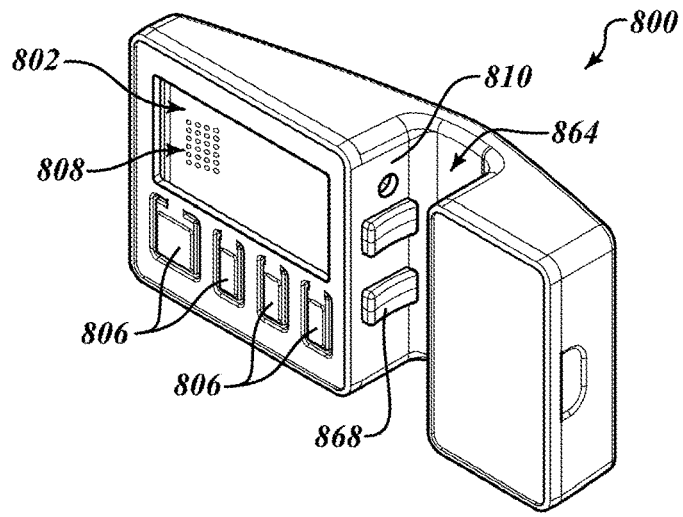
FIGS. 8A, 8B, and 8C show various views of a monitoring device according to embodiments of the present disclosure.
Figure 8B:
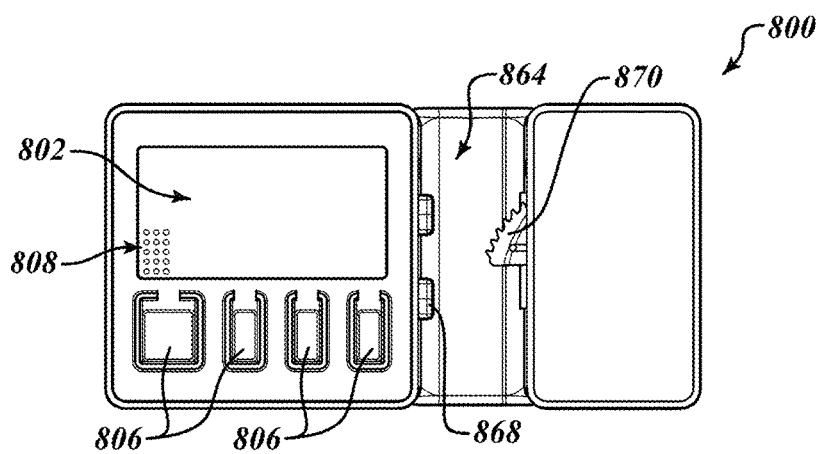
Figure 8C:
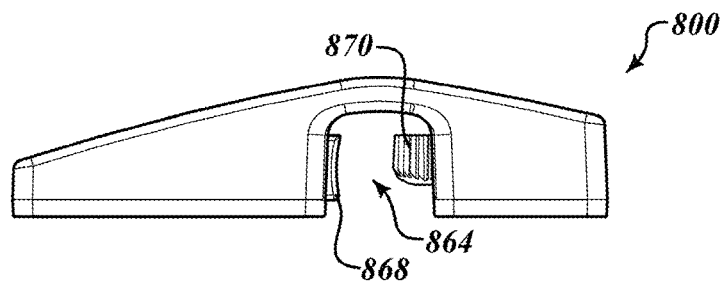

In some embodiments, including at least embodiments discussed in view of FIGS. 8A, 8B, and 8C, at least a portion of the drip chamber may be visible to a user when the monitoring device is affixed to the infusion set. Providing the user visibility to at least a portion of the drip chamber during operation of the monitoring device may enable the user to visually inspect fluid drops within the channel. In at least one of the various embodiments, the monitoring device is affixed to the chamber by employing a trench or channel that provides the user visibility to at least a portion of the drip chamber. In some embodiments, when infusion set 190 is suspended or otherwise repositioned, monitoring device 100 remains affixed to the drip chamber.

Figure 2:
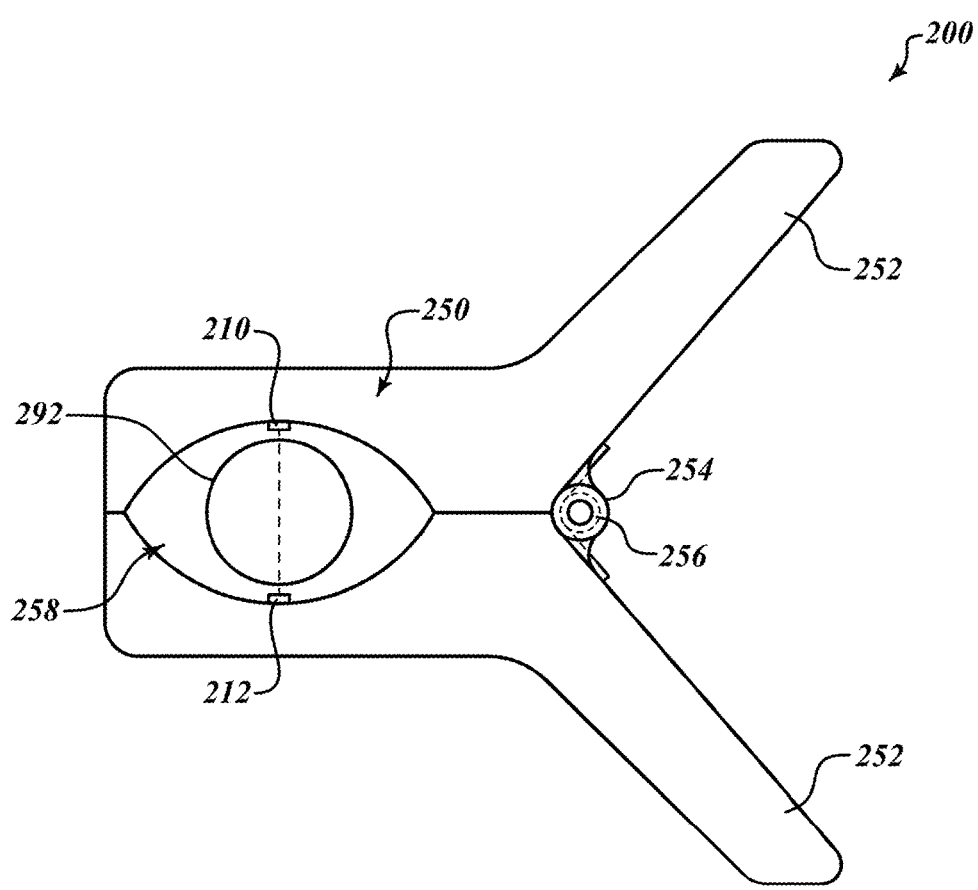
FIG. 2 shows a top-down view of a flow rate monitoring device affixed to a drip chamber according to embodiments of the present disclosure.

FIG. 2 shows a top-down view of an embodiment of flow rate monitoring device 200 affixed to drip chamber 292. Monitoring device 200 includes device body 250. Monitoring device 200 includes cavity 258. In some embodiments, cavity 258 may be a cavity, hole, trench, depression, or aperture within device body 250. In some embodiments, cavity 258 may include at least one inner surface.

When monitoring device 200 is attached to drip chamber 292, drip chamber 292 may be positioned within cavity 258. In at least one embodiment, cavity 258 may be configured and arranged to receive at least a portion of drip chamber 292. The at least one inner surface of cavity 258 may provide a gripping or otherwise frictional force that grips an outer surface of drip chamber 292. This gripping force may enable stabilizing the monitoring device 200 about drip chamber 292.

In some embodiments, the fit between the outer surface of drip chamber 292 and inner surface of cavity 258 may be snug and lack gaps. As shown in FIG. 2, in some embodiments, gaps between at least portions on the outer surface of drip chamber 292 and inner surface of cavity 258 may exist when monitoring device 200 is affixed to drip chamber 292. In some embodiments, monitoring device 200 may accommodate drip chambers of varying shapes and dimensions by outfitting the inner surface of cavity 258 with at least one of a compressible gripping material, camming device, or a textured portion.

Monitoring device 200 includes source 210 and detector 212. Source 210 may be enabled to emit EMR. In some embodiments, the operation of source 210 may allow for controlling at least the timing and/or the intensity of the emission of EMR from source 210. Detector 212 detects the EMR emitted by source 210 and generates a corresponding signal. In some embodiments, source 210 may be an LED. In some embodiments, source 210 may be enabled to emit EMR within a specified range of wavelengths or frequencies. In some embodiments, source 210 may be an infrared emitting diode (IRED).

In various embodiments, detector 212 may be a photodiode. Detector 212 may be enabled to detect the specified range of wavelengths or frequencies of EMR emitted by source 210. In some embodiments, detector 212 may be more sensitive to the specified range of wavelengths emitted by source 210 than to other wavelengths. For instance, if source 210 emits IR EMR, then detector 212 may be enabled to generate a more sensitive signal in the presence of IR EMR, than in the presences of other wavelengths of EMR, such as visible light.

In some embodiments, source 210 and detector 212 may be in opposition along the inner surface of cavity 258. When aligned in opposition, source 210 and detector 212 form an optical path across cavity 258. EMR emitted by source 210 and travelling along the optical path may be detected by detector 212. Such an optical path is shown across cavity 258 by the dotted line.

In some embodiments, drip chamber 292 may be at least partially transparent, semi-transparent, or translucent to the wavelengths of EMR emitted by source 210. When monitoring device 200 is affixed to drip chamber 292, an optical path across drip chamber 292 is formed. If no fluid is within the optical path, then at least a portion of the EMR emitted by source 210 is detected by detector 212. The portion of EMR emitted by source 210 and detected by detector 212 may generate a baseline detector signal, as will be described in conjunction with FIGS. 5A and 5B, below.

At least a portion of device body 250 may be configured as a clip, such as a tension- or spring-loaded clip. A spring loaded clip may be opened by overcoming the tension with an external force, such as a user opening the clip. In the absence of such an external force, the clip may be in a closed state. When drip chamber 292 is positioned within cavity 258, the tension or spring force of the clip may provide a stabilizing force to affix monitoring device 200 to drip chamber 292.

To provide leverage to a user in assistance in opening the clip, one or more clip handles 252 may be included with device body 250. In some embodiments, spring 256 may provide at least a portion of the force that closes the clip and affixes device 200 to drip chamber 292. During opening and closing of the clip, at least a portion of the clip may pivot about hinge 254.

Figure 3:
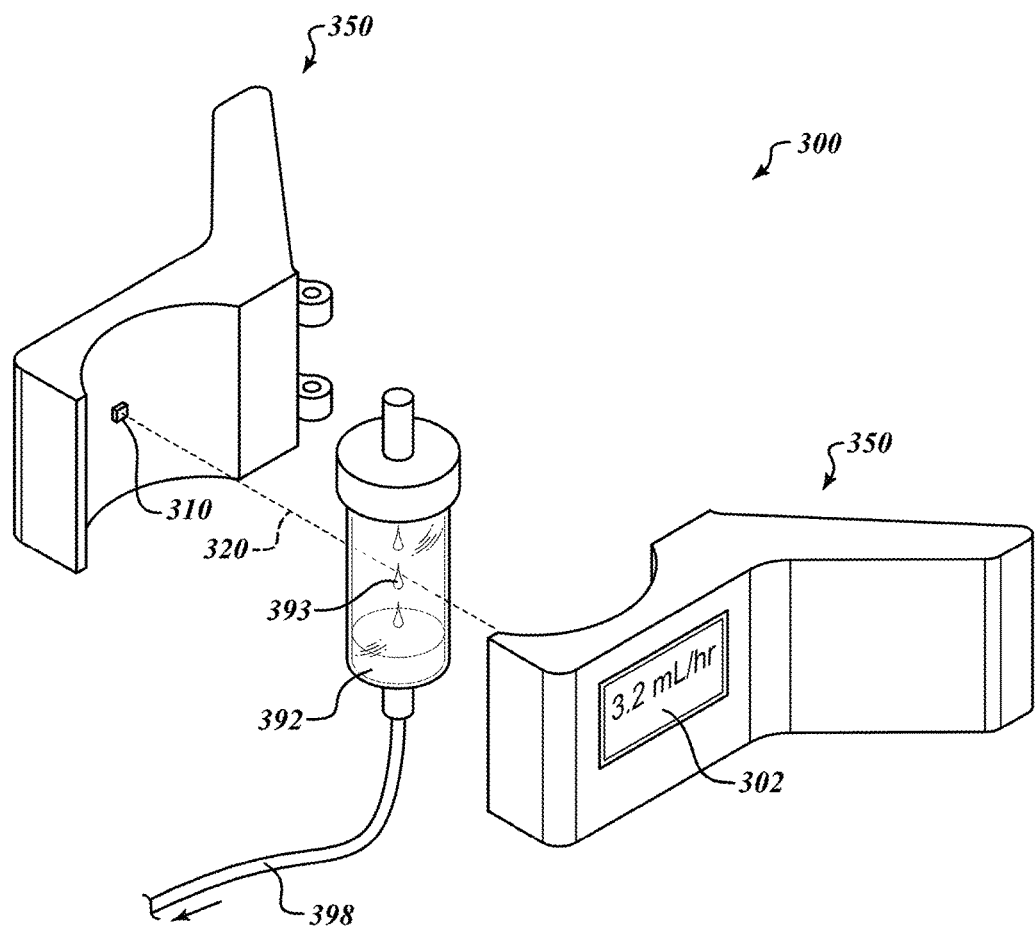
FIG. 3 shows an exploded view of a flow rate monitoring device with a drip chamber positioned within an optical path between a source and detector according to embodiments of the present disclosure.

FIG. 3 provides an exploded view of flow rate monitoring device 300 with drip chamber 392 positioned within the optical path 320 between source 310 and the corresponding detector (hidden from view). The dotted line demarcates optical path 320.

Drip chamber 392 is configured and arranged such that fluid entering drip chamber 392 from the top, drips as individual drops, and forms a pool of fluid at the bottom of drip chamber 392. Fluid in the pool then flows out of drip chamber 392 and into fluid output 398. Fluid flowing through fluid output 398 is ultimately delivered to the target.

During steady state operation of an infusion set, the volume of the pool of fluid at the bottom of drip chamber 392 remains approximately constant. In such steady state operation, the rate of fluid delivered to the target through fluid output 398 (in units of mL per unit time) may be determined based on a ratio of the number of fluid drops falling in drip chamber 392 per unit time to an appropriate drip factor in units of gtt/mL. An accumulated volume of fluid delivered to the target may similarly be determined based on a ratio of a total number of fluid drops that have fallen in drip chamber 392 to the drip factor.

Three individual fluid drops are shown at various points falling from the top of drip chamber 392 towards the pool of fluid at the bottom of drip chamber 392. The amount of time an individual drop takes from first beginning to drop from the top of drip chamber 392 to the time it reaches the pool at the bottom of drip chamber 392 may be referred to as drop time-of-flight.

Monitoring device 300 is configured and arranged, such that when affixed to drip chamber 392, each fluid drop passing through drip chamber 392 will pass through optical path 320 during a portion of the drop's time-of-flight. Fluid drop 393 is shown within optical path 320. The time period during which a drop is within optical path 320 may be referred to as the drop's line-of-sight period. The length of a drop's line-of-sight period may be referred to as the drop's line-of-sight time.

In some embodiments, the fluid drops passing through drip chamber 393 are not completely transparent to at least a portion of the EMR wavelengths emitted by source 310. At the very least, the combination of drip chamber's 392 walls and fluid drop 393 is less transparent to the emitted EMR than drip chamber's 392 walls without fluid drop 393 in optical path 320. Thus, during the drop's line-of-sight period, fluid drop 393 will at least partially inhibit EMR emitted from source 310 from travelling across optical path 320. For instance, fluid drop 393 may partially obscure or refract EMR within optical path 320 during its corresponding line-of-sight period.

Because EMR emitted from source 310 will be at least partially inhibited during fluid drop's 393 line-of-sight period, a response of the detector will vary, producing a signal different than that of the signal produced when no fluid is within optical path 320. The signal produced by the detector when fluid is not within optical path 320 may be referred to as the detector's baseline signal.

As provided in more detail below in regards to FIGS. 5A and 5B, monitoring device 300 may be enabled to use the varying signal generated by the detector to detect in real time, each individual fluid drop as it passes through drip chamber 392. Based on at least the detection of each individual fluid drop, monitoring device 300 may be enabled to determine a total number of fluid drops that have passed through drip chamber 392. By applying the appropriate drip factor to convert number of drips into volume of fluid, monitoring device 300 may determine a total volume of fluid delivered to the target through fluid output 398.

In various embodiments, monitoring device 300 may be enabled to determine the amount of time between each successive detected fluid drop in drip chamber 392. By detecting a plurality of individual drops over time, monitoring device 300 may determine a fluid drop rate, such as the number of drops per unit time. By applying the appropriate drip factor, monitoring device 300 may determine a volumetric fluid flow rate delivered to the target through fluid output 398. As provided in more detail with regards to FIG. 6, monitoring device 300 may determine a rolling average and an associated stability of the number of drops per unit time and the volume of fluid per unit time.

In at least one of the various embodiments, monitoring device 300 may determine if a determined drop or volumetric flow rate falls outside of a specified range, such as +−10% of a nominal or target value. Such instabilities may occur when a patient changes positions, the IV bag changes positions, tubing pressure changes, the position of a roller clamp is accidently altered, the infusion set becomes clogged, the IV bag is depleted and such.

Monitoring device 300 may provide a user with these determinations and additional information by employing display unit 302. In some embodiments, monitoring device 300 may provide alerts to a user. Such alerts may be triggered when determinations, such as instabilities in a drop or fluid flow rate, do not match target values within a specified range. Alerts may be provided when an accumulated total target volume of fluid has been delivered or the total target volume has been exceeded. Alerts may be provided through display device 302 and/or through an audio interface, such as a speaker. In at least some embodiments, alerts provided to the user may include visual alerts, such as alerts provided by an LED that emits at least optical frequencies of EMR or other such sources of light, including light bulbs or optical lasers. Alerts may be provided by rapidly pulsing audio or visual signals, such as a strobe light or a siren. Users may provide monitoring device 300 with target values for such metrics that are monitored, through user input interfaces, such as user input interface 106 of FIGS. 1A and 1B.

Some embodiments may be networked to remote devices and supply users of the remote devices with such information and alerts. Some embodiments of monitoring device 300 may include non-volatile memory devices that enable the creation of log files including one or more metrics determined and monitored by monitoring device 300. Log files may include values of user inputs, such as target volume or target flow rates. Log files may include other data, such as the amount of time that fluid was flowing through a drip chamber, time stamps for each individually detected drop, drop waveforms, and other diagnostics, acquired data, and operating conditions.

By employing a networked monitoring device, data may be provided to remote devices. Such provided data may be used by remote devices to generate log files. These log files may be archived for future access and may become part of a patient's medical history. These log files may be used as input data for clinical tests or other research or industrial purposes. For example, log files may be employed in the production of or research regarding energy sources, such as biofuels.

Figure 4:
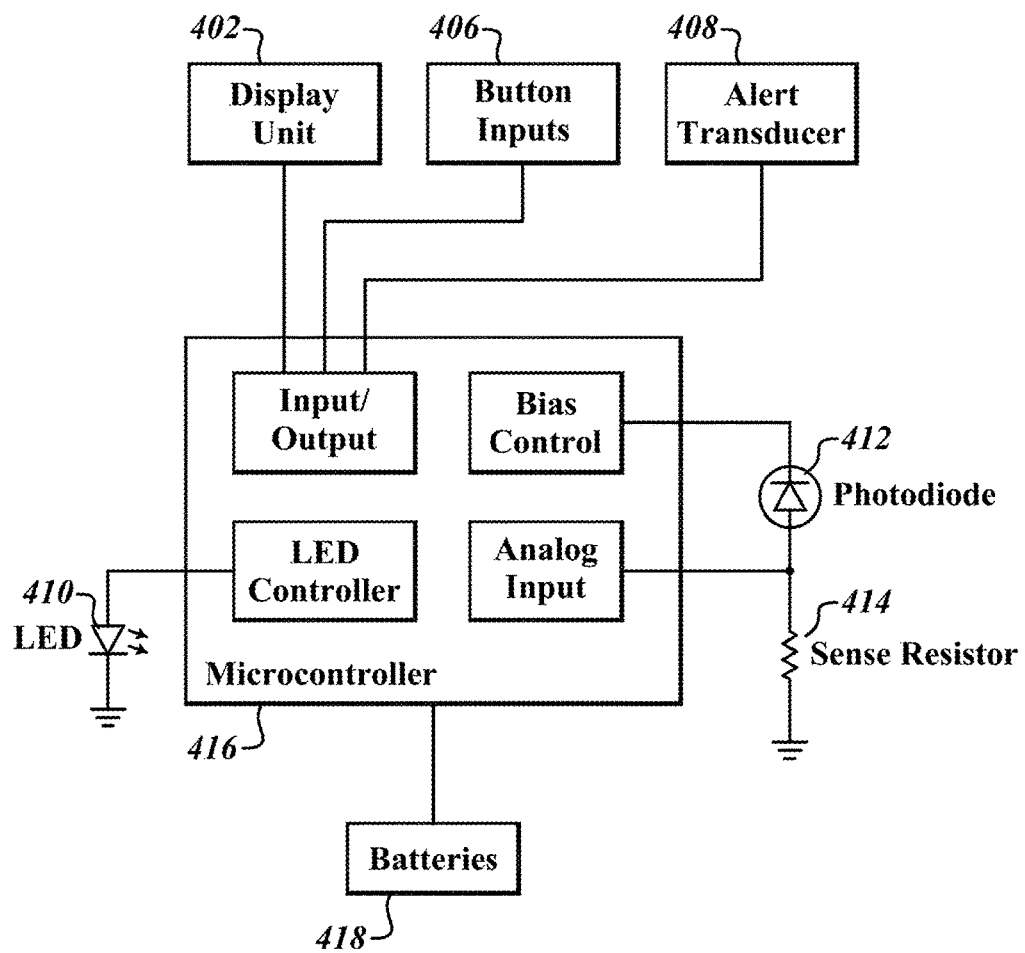
FIG. 4 shows a block level diagram of electronic components included in various embodiments of a flow rate monitoring device described in the present disclosure.

FIG. 4 shows a block level diagram of components included in various embodiments of flow rate monitoring devices described throughout the present disclosure. One such monitoring device may be monitoring device 100 of FIG. 1. In some embodiments, a monitoring device may include a processor device. In at least one of the various embodiments, a processor device may include a programmable microcontroller, such as microcontroller 416.

A monitoring device includes a source. In some embodiments, a source may include LED 410. LED 410 may be an infrared (IR) LED, such as an IRED. At least one terminal of LED 410 may be tied to ground. A monitoring device may include a detector. In some embodiments, detector may include photodiode 412. Photodiode 412 may have a greater sensitivity to IR wavelengths than to wavelengths within the visible light spectrum. In some embodiments, sense resistor 414 may be used in conjunction with photodiode 414. Sense resistor may be between photodiode 412 and ground.

In some embodiments, microcontroller 416 may control the operation of at least one of LED 410 and photodiode 412. Such controls may include controlling a pulsing of biasing currents used in the operation of LED 410 and photodiode 412. Furthermore, microcontroller 416 may monitor one or more signals from photodiode 412, including at least an EMR detection signal generated by photodiode 412 and in response to detecting EMR emitted from LED 410.

The EMR detection signal may be a digital signal. However, in at least some embodiments, the EMR signal may be an analog signal. If the EMR detection signal is an analog signal, the EMR detection signal may be digitized before being provided to microcontroller 416. In other embodiments, the EMR detection signal may be provided to microcontroller 416 as an analog signal. In some embodiments, no pre-amplification may be required of the EMR detection signal prior to being provided to microcontroller 416. In these embodiments, the ability to provide microcontroller 416 the EMR detection analog signal without pre-amplification reduces the total number of components required for manufacturing a monitoring device. This reduction in component count may result in reducing cost and/or complexity of the monitoring device.

Monitoring devices may operate in a "continuous mode" or a "sample mode." In some embodiments, at least one of LED 410 and photodiode 412 may be operated at a 100% duty cycle during the operation of the monitoring device. In these "continuous mode" embodiments, fluid drop detection measurements may be made continuously.

In order to reduce operating power requirements, at least one of LED 410 and photodiode 412 may be operated at less than a 100% duty cycle. In such "sample mode" embodiments, fluid drop detection measurements may be made periodically or in samples rather than continuously. Thus, sample measurements may be made at a predetermined frequency.

The amount of time an individual fluid drop, such as fluid drop 393 of FIG. 3, is within the monitoring device's optical path, such as optical path 320, may be referred to as the drop's line-of-sight time. In some embodiments, time between consecutive samples, or sample period, may be less than a drop's line-of-sight time. In at least one of the various embodiments, the sample period may be significantly less than a drop's line-of-sight time. As will be shown in conjunction with FIGS. 5A and 5B, employing a sample period significantly less than a drop's line-of-sight time allows for the generation of a drop's waveform or time profile.

In some embodiments, LED 410 and photodiode 412 are operated for only a fraction of a sample period for each sample measurement. For instance, for a sample frequency of 1 kHz, a sample measurement is obtained every 1 millisecond (ms). In some embodiments, 1 ms is significantly less than any individual drop's line-of-sight time. To sample the transparency of optical path 320 during a single sample measurement, bias current is supplied to LED 410 and photodiode 412 for a length of time referred to as an operation time. The operation time may be less than the sample period. For instance, for a sample period of 1 ms, the bias current may be supplied to LED 410 and photodiode 412 for only about 10 microseconds. An operation time of 10 microseconds results in an operational duty cycle of (10 microsecond)/(1 ms), or 1%.

"Sample mode" embodiments may enable monitoring devices with significantly lower power consumption requirements because biasing currents are only being supplied to the source and detectors for a small fraction of the time. Operation times may be based on one or more characteristics such as source and detector rise and fall times, operating speed of a processor device, optical transparency of the fluid and/or drip chamber walls, length of drip chamber, response times of various components and/or circuits included in the monitoring device, and the like.

It is understood that the numerical values for sample frequency, sample period, operation time, as well as all other numerical values used herein are for illustrative purposes only, and the disclosure is not so constrained by the values provided herein. Rather, these values are chosen for their illustrative purposes. In some embodiments, sample periods and the like may be varied to account for detector response times, length of drip chambers, characteristics of the fluid, characteristics of sources/detectors such as rise/fall times, and the like.

In some embodiments, microcontroller 416 may control the pulsing of biasing currents for LED 410 and photodiode 412. Some embodiments may be enabled to operate in both "continuous" and "sample" modes. In such embodiments, a user may be enabled to select which mode to operate in, as well provide programmable operational parameters such as sampling frequency, duty cycles, and the like.

Various embodiments may include a power supply. The power supply may supply power to various components, such as microcontroller 416, as well as other components. In some embodiments, the power supply may be an internal power supply, such as battery 418. Battery 418 may be replaceable. Furthermore, battery 418 may be rechargeable. Some embodiments may include more than one battery to provide redundancy. Some embodiments may account for an external power supply, such as wall mounted sockets. Some embodiments may be enabled to employ both an external and an internal power supply, depending on the needs of a user and the context of operation. For instance, some monitoring devices may be powered by a wall socket, and also include a backup battery in the event of a loss of power to the wall socket. In at least one of the various embodiments, the power source may include a photovoltaic cell, such as a solar cell.

Monitoring devices may include display unit 402. Display unit 402 may be employed to provide information to a user. Such information may include, but is not limited to, determined fluid flow rates, fluid drop rates, percentage or absolute amount of battery power remaining, the drip factor currently used by the monitoring device, total accumulated drops, total accumulated fluid flow, and the like. Microcontroller 416 may control at least a portion of display unit 402.

Monitoring devices may include a user input interface. A user input interface may include button inputs 406. Button inputs 406 may be used by a user to provide the device with various user inputs, such as drip factor, target fluid drop rate, target fluid flow rate, target total accumulated fluid flow, etc. In some embodiments, a user may toggle between "continuous mode" and "sample mode" of operation by employing button inputs 406. In some embodiments, a user may provide a monitoring device with a target duty cycle or other such input information by employing button inputs 406.

Monitoring devices may include an audio interface, such as alert transducer 408. Alert transducer 408 may be a speaker used to provide audio alerts and other audio information to a user. Microcontroller 416 may communicate with display unit 402, button inputs 406, and alert transducer 408 and supply inputs and outputs to these and other devices.

Although not shown, it is understood that various other components, such as charge pumps, may be used in embodiments. Digital memory devices may be included in various embodiments. Memory devices may be volatile or non-volatile memory devices. Memory devices may include, but are not limited to RAM, ROM, EEPROM, FLASH, SRAM, DRAM, optical disks, magnetic hard drive, solid state drives, or any other such non-transitory storage media. Memory devices may be used to store various information, including but not limited to programmable user inputs, monitored metrics, log files, or operational parameters.

Although not shown, it is understood that various embodiments of monitoring devices may include a network transceiver device. Such network transceivers may be enabled to communicate with other devices over a wired network or a wireless network. Such transceivers may be enabled with Wi-Fi, Bluetooth, cellular, or other data transmission and networking capabilities. In such embodiments, monitoring devices may be enabled to communicate with other devices. These other devices may include remote computer devices, such as servers, clients, desktops, and mobile devices.

Users may supply inputs to the monitoring device by the remote use of these networked computer devices. Furthermore, users may be enabled to monitor, in real time, information supplied by the monitoring devices, through the use of remote computing devices. Health care providers may be enabled to remotely monitor patients from afar. For instance, doctors or nurses, in one area of a hospital may be able to remotely monitor the IV drips for patients located in other areas of the hospital. Mobile devices, such as tablets or smartphones may be employed for such remote, real-time monitoring.

Also, the networking capabilities may enable data logs for patients to be generated and archived. These data logs, or log files, may become part of a patient's medical history. Furthermore, these log files may be employed as evidence regarding a standard of care provided to the patient.

Figure 5A:
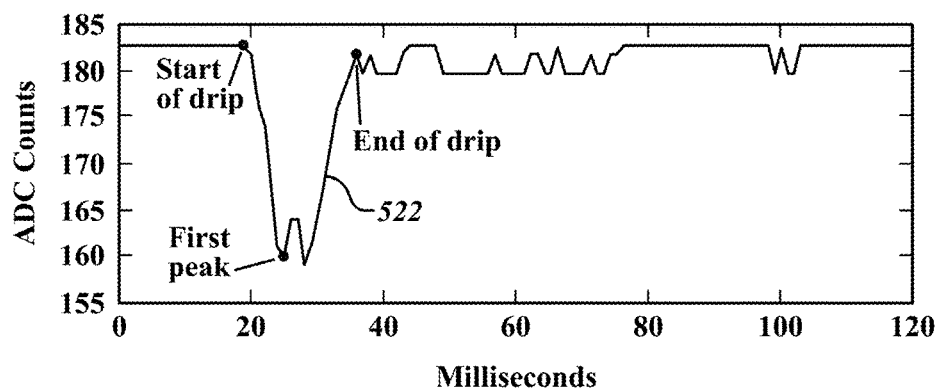
FIGS. 5A and 5B show time series of generated waveforms based on EMR detection signals as described in the present disclosure.
Figure 5B:
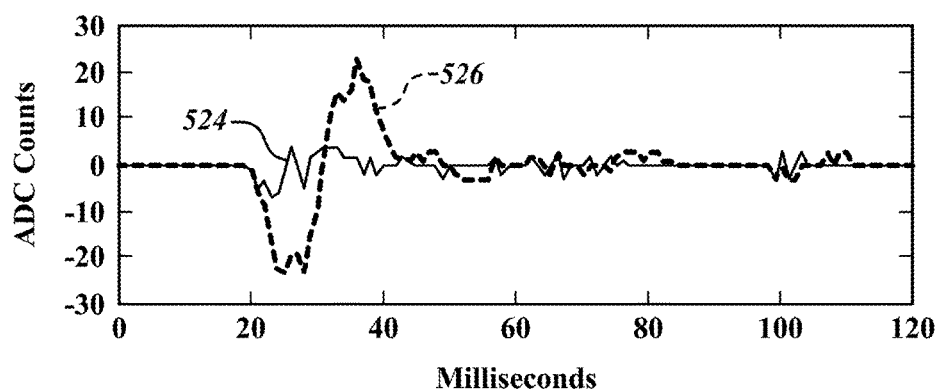

FIGS. 5A and 5B show time series plots of generated waveforms based on EMR detection signals. In some embodiments, a waveform may include a temporally ordered plurality of points, each corresponding to a detector signal. Each point in a waveform may include a time coordinate and a detector signal coordinate. Because the points are temporally ordered, characterization of points as prior, current, and subsequent point are well defined. Also, a distance between points, such as a time distance between points is well defined.

In FIGS. 5A and 5B, the unprocessed EMR detection signals may be analog signals from a detector, such as photodiode 412 of FIG. 4. The analog signals may be digitized prior to the generation of waveforms. In some embodiments, the digitization may occur within a processor device, such as microcontroller 416 of FIG. 4. A digitization process may employ an Analog-to-Digital Converter (ADC), internal to microcontroller 416. FIG. 5A shows a pre-processed drop waveform 522. The x-axis represents the time of a sampled detector reading in milliseconds. The y-axis represents an ADC value based on the signal generated by the detector at each sampled time.

In FIG. 5A, the start of a fluid drop, such as fluid drop 393 of FIG. 3, entering an optical path, such as optical path 320 of FIG. 3, is marked at approximately 20 ms. Furthermore, the time that the fluid drop exits the optical path is marked at approximately 36 ms. Thus, the drop line-of-sight time is approximately 16 ms.

Note the variance in value of waveform 522 during the line-of-sight period. A two peak structure may be characteristic of some fluid drops. Note the two peak structure in waveform 522, where the first peak is marked at approximately 27 ms, and the second peak occurs at approximately 29 ms. This variance in the digitized signal value is due to the fluid drop inhibiting EMR emitted by a source, such as LED 410, from flowing across the optical path.

Also note the baseline signal, with an ADC count of approximately 183, corresponding to the uninhibited flow of the EMR across the optical path. Noise fluctuations are also shown on drop waveform 522. In some embodiments, these noise fluctuations may be filtered using hardware and/or software based filters.

In some embodiments, drops may be detected by employing a processor device, such as microcontroller 416 of FIG. 4, to analyze drop waveforms in real time, such as exemplary drop waveform 522. Some embodiments may utilize a method of analyzing drop waveforms that includes a comparison of the waveform at each sample to an absolute threshold, such as a calibration threshold or an averaged or filtered value of the baseline signal, shown in waveform 522.

Other embodiments may compare at least a portion of the points in waveform 522 to other points in waveform 522. In such embodiments, the detector signal at various sample times may be employed to generate difference waveforms. Such difference waveforms may result in difference signals that are characteristic to the detection of fluid drops. For instance, the detector signal (or ADC count) at each sample may be compared to the detector signal (or ADC count) from a prior sample. An amount of time between the time corresponding to the current sample and the time corresponding to the prior sample may be referred to as lag time.

A lag time difference waveform may be determined by first generating a pre-processed waveform, such as waveform 522. Subsequent to generating pre-processed waveform 522, a difference between each point included in at least a portion of the points on pre-processed waveform 522 and a prior point on pre-processed waveform 522 may be determined, where the two points used to generate the difference are separated by a time distance equal to the lag time.

FIG. 5B shows lag time difference waveform 524, which is a simple difference waveform. Simple difference waveform 524 was generated using a lag time equivalent to the sample period. In other words, each instance of the detector signal is compared to the immediate prior sample. For simple difference waveform 524, the sample period is equal to the lag time (1 ms) and the drop line-of-sight time is approximately 16 ms. Detecting a fluid drop from a simple difference waveform may prove difficult because unless the absolute values of the time derivative of the pre-processed waveform 522 are large enough, the liquid drop signal resulting from a simple difference waveform may be small, as shown in simple difference waveform 524.

Other choices of lag time may be more advantageous. In order to produce a better signal-to-noise ratio, a larger lag time may be employed. Such larger lag times may produce difference signals more characteristic of a fluid drop, resulting in a suppression of false positive and false negative fluid drop detections. Some embodiments may employ a lag time approximately equal to half a drop's line-of-sight time. Such a value may result in a larger time difference signal. Such a value may enhance the likelihood of successfully detecting a fluid drop. This is because the peak structure of the unprocessed waveform is compared to the baseline signal of the waveform, resulting in a larger time lag difference signal that is indicative of a fluid drop.

For instance, lag time difference waveform 526 was generated from waveform 522 by using a lag time of 8 ms. Note the amplitude of the signals in lag time difference waveform 526 with simple difference waveform 524. The greater signal amplitude of time difference waveform 526 may result in better drop detection. Also note both the positive and negative structure of waveform 526. The negative and positive peaks of lag time difference waveform 526 result from the comparison of the peak structure of pre-processed waveform 522 in comparison to the baseline detector signal prior to and subsequent to the drop's line-of-sight period, respectively. This adjacent negative and positive peak structure associated with an appropriate choice of lag time may be a characteristic signal of a fluid drop detection. Thus, such appropriate choices for a lag time may result in a better signal to noise ratio and/or an increase in drop detection accuracy; including at least suppressing both false positive and false negative detections.

Waveform 526 may not be sensitive to long-term changes of signal value, but it largely retains the high signal to noise ratio of waveform 522. The waveform 522 may exhibit a large signal difference between the signal baseline and the negative peak. However, the specific ADC count values of the baseline and the peak will vary based on a variety of factors including but not limited to source brightness, shape, and material of the drip chamber, ambient light, drip position, and condensation on the drip chamber. No single threshold value for detecting a drip will be robust to changes in these environmental factors.

The waveforms 524 and 526 are not sensitive to long-term changes in signal value, so the above factors do not affect the signal. However, the signal to noise ratio of waveform 524 is low, which may lead to problems with false positives and negatives. Waveform 526 is not sensitive to long-term changes of signal value, but it largely retains the high signal to noise ratio of waveform 522.

In some embodiments, the lag time is chosen to be longer than a fall and/or rise time of the detector. In at least one of the various embodiments, an employed lag time is longer than several sample periods, but shorter than the drop line-of-sight time. For instance, a lag time of 8 ms is shorter than a line-of-sight time of 16 ms (and is approximately half the drop's line-of-sight time), but longer than a sample period of 1 ms, as shown in waveforms 526. A lag time longer than the drop line-of-sight time may fail to detect fluid drops. In some embodiments, the lag time may be varied depending on the particular use of a monitoring device. In some embodiments, a user may be enabled to provide a lag time to use during a particular operation.

In some embodiments, a lag time difference waveform, such as lag time difference waveform 526, generated based on an appropriate lag time value, may be employed in detecting each individual drop. By employing at least a processor device, such as microcontroller 416 of FIG. 4, drop detection may be performed in real time, as the drop is falling in the drip chamber. Lag time difference waveforms may be analyzed to detect the fluid drops. In various embodiments, drop detection may be based on the shape of a plurality of lag time difference waveforms generated by employing an appropriate lag time value.

Some embodiments may employ a lockout method to enable a vetoing of false positive drop detections. It is possible for a detector signal to present a drop profile at more than one instant in time. For instance, if the time difference between the detection of a first drop and a second drop is below a lockout threshold, then at least one of the detections is determined as a spurious detection. A spurious detection event may trigger the vetoing of at least one of the two drop detections.

In some embodiments, the waveforms corresponding to vetoed, or lockout detections, may be included in a log file for future analysis. In some embodiments, the detection of a plurality of lockout events within a minimum amount of time may signal that the drop rate is unstable, or that the drops or flowing too quickly within the drip chamber to enable individual drop detections. Some embodiments may provide a user with an audio or visual alert in the event of one or more lockout events.

The lockout threshold or period may be chosen to be longer than a drop line-of-sight time, but shorter than an average drop rate. In some instances, a user may supply the lockout threshold. In some embodiments, the lockout threshold may be varied to account for a current average drop rate.

Figure 6:
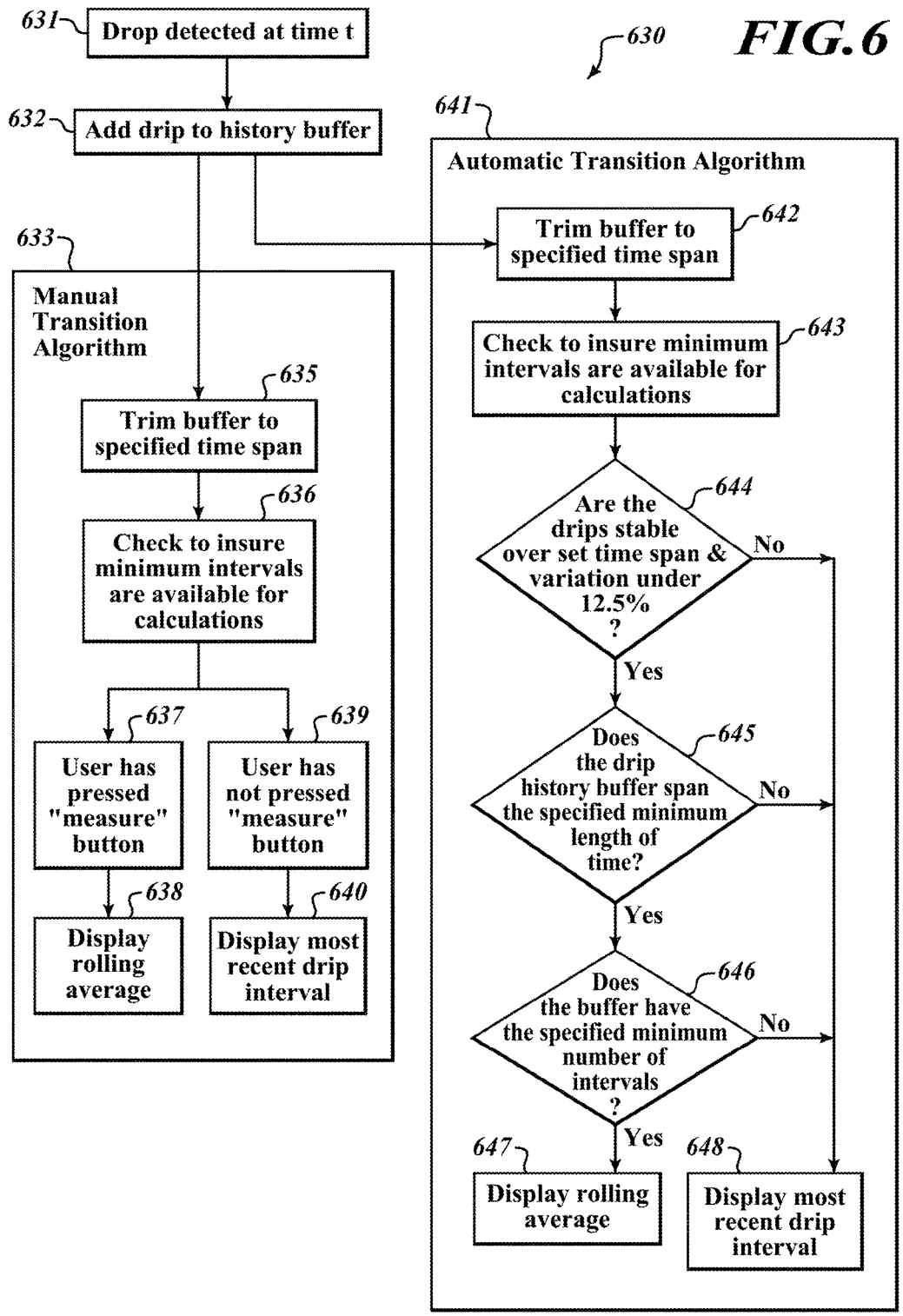
FIG. 6 shows embodiments of methods for operating a monitoring device.

FIG. 6 shows embodiments of method 630 for operating a monitoring device. Methods, such as method 630, may be performed by a processor device, such as microcontroller 416 of FIG. 4. A processor device may execute instructions that perform actions. At block 631, a drop is detected within a drip chamber, such as drip chamber 392 of FIG. 3, at time t. The drop may be detected using various methods, such as, but not limited to, the various embodiments discussed in reference to FIGS. 5A and 5B. If the drop is not vetoed as a lockout event, then method 630 may proceed to block 632.

At block 632, the detected drop is added to a drop history buffer. In some embodiments, the buffer may be stored in at least a memory device included in the monitoring device. The memory device may be a volatile or non-volatile memory device. Adding the detected drop to the drop history buffer may include adding a detection time to the buffer. In some embodiments, a drop line-of-sight time corresponding to the added drop may be added to the buffer. In at least one of the various embodiments, at least a portion of the detector signal associated with the added drop may be added to the buffer. At least one waveform, such as any of 522, 524, or 526 of FIGS. 5A and 5B may be added to the buffer. A total drop count associated with the detected drop may be added to the buffer. In some embodiments, the buffer includes a plurality of previously detected drops.

If a monitoring device is operated in a manual transition mode, method 630 branches to manual transition method 633 and proceeds to block 635. If the monitoring device is operated in automatic transition mode, method 630 branches to automatic transition method 641 and proceeds to block 642. In at least one of the various embodiments, a user may be enabled to select manual transition mode or automatic transition mode by employing a user input interface, such as user input interface 106 of FIGS. 1A and 1B.

At block 635 and block 642, the drop history buffer is trimmed to a specified time span. The specified time span may depend on an available size of the buffer, such as the amount of memory allocated for the buffer. The buffer size may be resized to accommodate the specified time span. If the addition of the drop detected at block 631 to the buffer would induce a buffer overflow, at least one drop may be removed from the buffer. The buffer may be a first-in first-out (FIFO) buffer, so that the removed drop is the least recent drop in the drop history buffer. The buffer may be trimmed or expanded so that a specified maximum or minimum number of drops are included in the history buffer.

At block 636 and block 643, a check is performed to insure minimum intervals are available for further determinations. For instance, if a rolling drop rate average is to be determined, a check may be performed to insure that a minimum number of drops are included in the buffer. In some embodiments, a check may be performed to insure that a minimum time between the most recent and least recent drops in the buffer exists. In some embodiments, a check may be performed to insure that a minimum time between successive drops in the buffer exists. These and other checks may be performed to insure the statistical significance or stability of further determinations.

In some embodiments, a rolling average may be determined. In at least one of the various embodiments, a rolling average may be based on a ratio of a total number of detected drops in the buffer to a total amount of time between the detections. For instance, a total amount of time between the detections may be based on a difference of the detection time of the most recent drop in the buffer and a detection time of the least recent drop in the buffer. In some embodiments, the rolling average may be determined in various units. For instance, the rolling average may be determined in drops per unit time, or time between drops. In at least one of the various embodiments, the rolling average may be determined in volume of fluid per unit time or time per unit of volume. It is to be understood that other methods for determining a rolling average may be employed.

If a user has indicated to measure the drop rate, then method 633 proceeds to block 638. For instance, a user may indicate to measure the drop rate by activating a measure mode through a user interface, such as user interface 106 of FIGS. 1A and 1B. At block 638, the determined rolling average may be displayed. Displaying the rolling average may be enabled by employing a display unit, such as display unit 102 of FIGS. 1A and 1B.

If a user has not indicated to measure the drop rate, then method 633 proceeds to block 640. At block 640, the most recent time interval may be displayed. The most recent time interval may be based on at least the detection times of the two most recent drops in the drop history buffer.

At decision block 644, a determination is performed based on at least a drip stability. The drip stability may be determined based on a comparison of a plurality of distances between detection times of successive drops included in the drop history buffer. If the drip stability is less than a predetermined threshold, method 641 proceeds to block 648. An illustrative, but non-limiting or non-constraining value of a stability threshold is a variation of 12.5%. At block 648, as with block 640, the most recent time interval may be displayed. Otherwise methods 641 proceeds to decision block 645.

At block 645, a determination is performed based on whether the drop history buffer spans a predetermined length of time. If the buffer does not span the predetermined length of time, method 641 proceeds to block 648. Otherwise, method 641 proceeds to decision block 646.

At block 646, a determination is performed based on whether the buffer has a predetermined minimum threshold of intervals. If the buffer does not have the predetermined threshold of intervals, method 641 proceeds to block 648. Otherwise, method 641 proceeds to block 647. At block 647, the determined rolling average is displayed.

Figure 7:
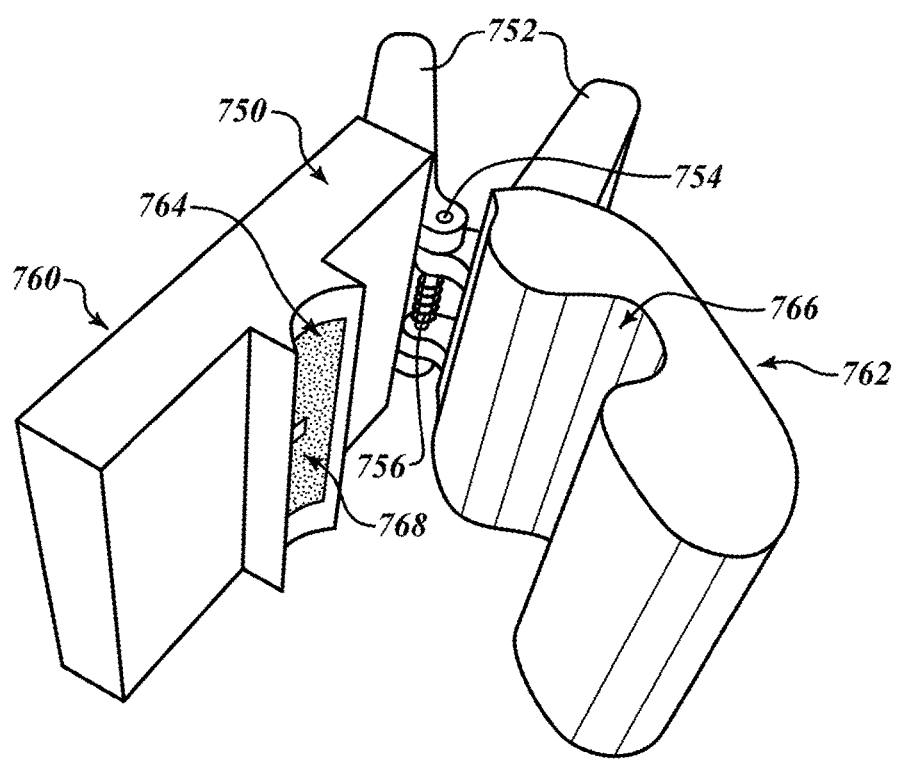
FIG. 7 shows an embodiment of a clip-style monitoring device body according to embodiments in the present disclosure.

FIG. 7 shows one embodiment of device body 750 included in some embodiments of a monitoring device. Device body 750 may be opened and closed. As shown in FIG. 7, device body 750 is an open state. At least a portion of device body 750 is enabled as a clip that can be opened by the application of a force. Clip handles 752 may be actuated by an actuating force to open device body 750. Clip handles 752 may provide leverage for a user to provide the actuating force required to open device body 750. During an opening or closing operation, portions of device body 750 may pivot about hinge 754.

When the actuating force is not applied to clip handles 752, device body 750 may be in its closed state. Spring 756 may supply the force to close the device. Device body 750 may include a first wing 760 and a second wing 762. First wing 760 and second wing 762 may be affixed about hinge 754. First wing 760 may include a first trench 764. Second wing 762 may include a second trench 766.

When device body 750 is in a closed state, first trench 764 and second trench 766 may be aligned to form a cavity, such as cavity 258 of FIG. 2. When device body 750 is affixed to a drip chamber, such as drip chamber 292 of FIG. 2, at least a portion of the drip chamber may be received by the cavity formed by the alignment of first trench 764 and second trench 766. At least one of first trench 764 and second trench 766 may include textured material to enable gripping of the drip chamber.

Figure 9:
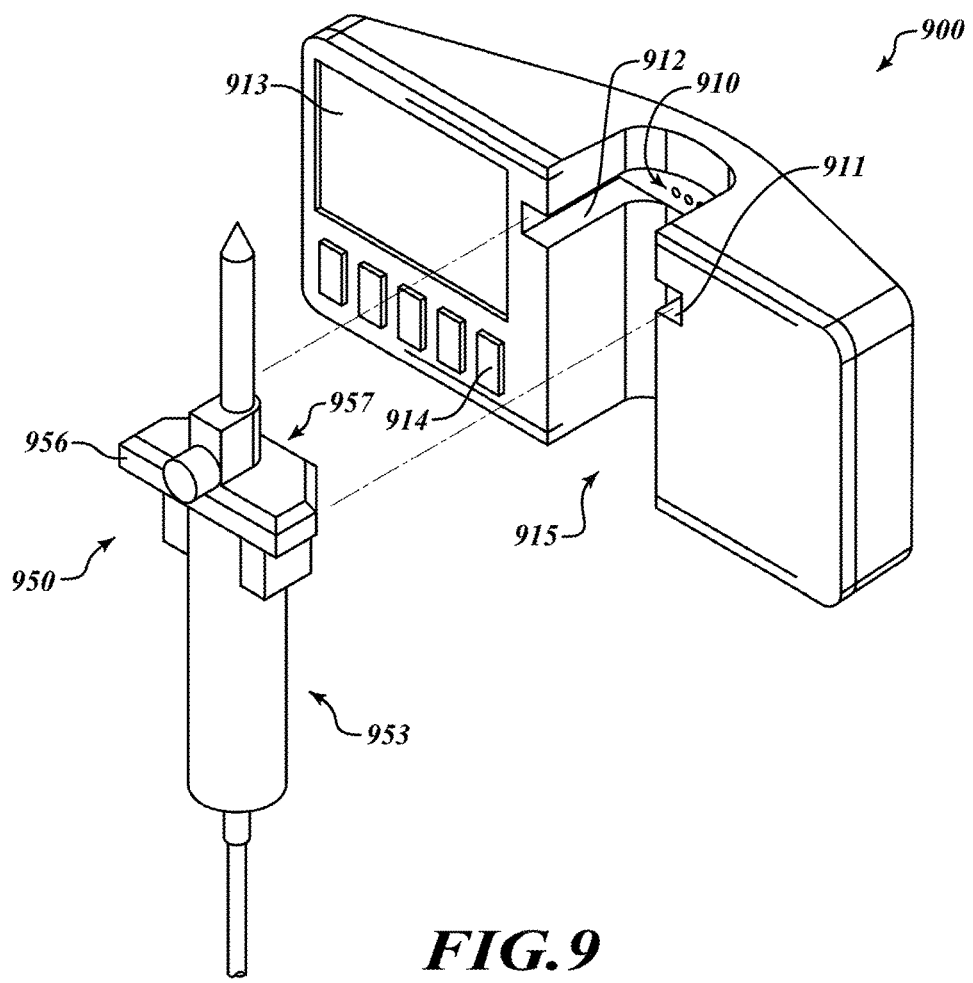
FIG. 9 is an exploded perspective view of a preferred monitoring system having a separate monitoring device and drip chamber with sensor housing.
Figure 18:
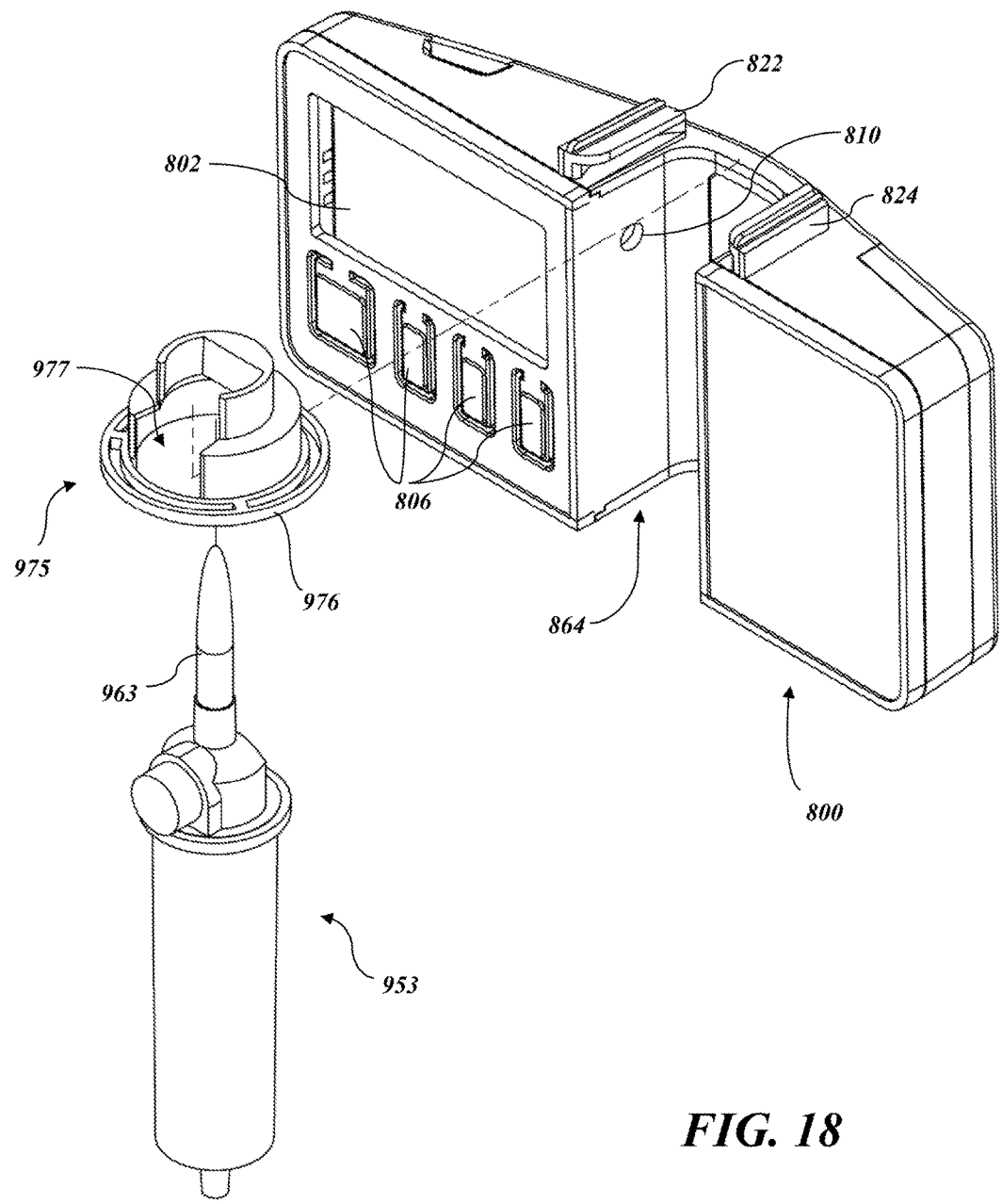
FIG. 18 is a perspective exploded view of a tubing set with drip chamber, shown with a collar for attachment to a monitoring device.
Figure 19:
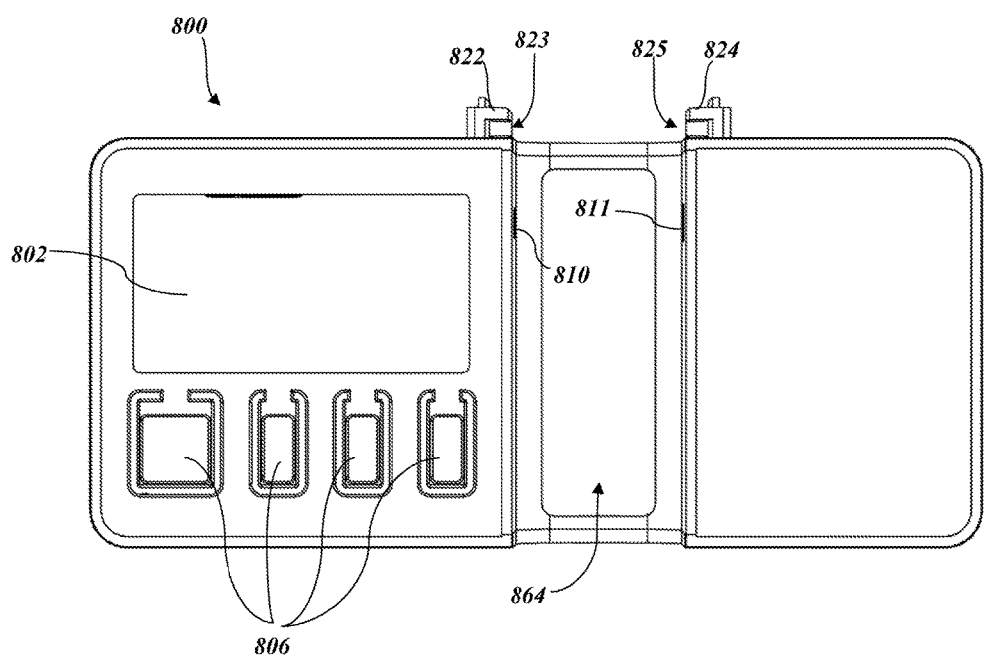
FIG. 19 is a front elevational view of a preferred monitoring device.

FIGS. 8A, 8B, and 8C show various views of embodiments of flow rate monitoring device 800. Monitoring device 800 may include display unit 802, user input interface 806, and user audio interface 808. A monitoring device 900 is also shown in FIG. 9 in which the tubing set 953 incorporates a mounted sensor device body 953. A monitoring device 800 is also shown in FIGS. 18 and 19, as with the device 800 of FIGS. 8A-c, incorporating the sensors in the monitoring device while providing a mechanism for attaching the tubing set in the manner of the channels illustrated in FIG. 9 and described below.

The monitoring device 800 may include an outer case having a channel. Some embodiments may include trench 864. When monitoring device 800 is affixed to a drip chamber, such a drip chamber 192 of FIG. 1, at least a portion of the drip chamber may fit snuggly in trench 864. At least one inner surface of trench 864 may include textured material 868 to assist in gripping the drip chamber. In some embodiments, at least one inner surface of trench 864 may include camming device 870 to assist in gripping the drip chamber. In some embodiments, textured material 868 and camming device 870 may be in opposition. In at least one embodiment, textured material 868 may be a compressible material that expands and contracts to accommodate drip chambers of various dimensions. In some embodiments, camming device 870 may be enabled to accommodate drip chambers of various dimensions. Camming device 870 may include ridges or teeth that enhance drip chamber gripping and friction.

Monitoring device 800 may include source 810. Source 810 may be positioned along at least an inner surface of trench 864. Although not shown, monitoring device 800 may include a detector. Source 810 and the detector may be in opposition along the inner surface of trench 864 to form an optical path across a drip chamber when monitoring device 800 is affixed to the drip chamber. This same arrangement is illustrated in FIGS. 18 and 19, and both the source 810 and detector 811 are visible in the elevational view of FIG. 19, showing the location of a corresponding detector in the monitoring device of FIGS. 8A-C.

In at least one of the various embodiments, the channel or trench 864 may receive a portion of the drip chamber when monitoring device 800 is affixed to the drip chamber. In some embodiments, because at least a portion of the channel or trench 864 is open, at least a portion of the drip chamber is visible to a user during operation of monitoring device 800. A user may be enabled to visually or manually inspect the dropping of the individual fluid drops during the monitoring of the fluid flow rate. Because at least a portion of the drip chamber is visible to the user, some embodiments may provide the user with visual feedback of the detected fluid drops. Due to visual feedback and in response to the determined fluid flow rate provided by the monitoring device, the user may precisely adjust or vary the flow rate, such as a manual operation of a roller clamp, like roller clamp 196 off FIGS. 1A and 1B, or other such adjusting means, to achieve the desired target flow rate.

FIG. 8A shows monitoring device 800 from a front-side view from an oblique angle. FIG. 8B shows monitoring device 800 from a front view. FIG. 8C shows monitoring device 800 from a top view.

Figure 10:
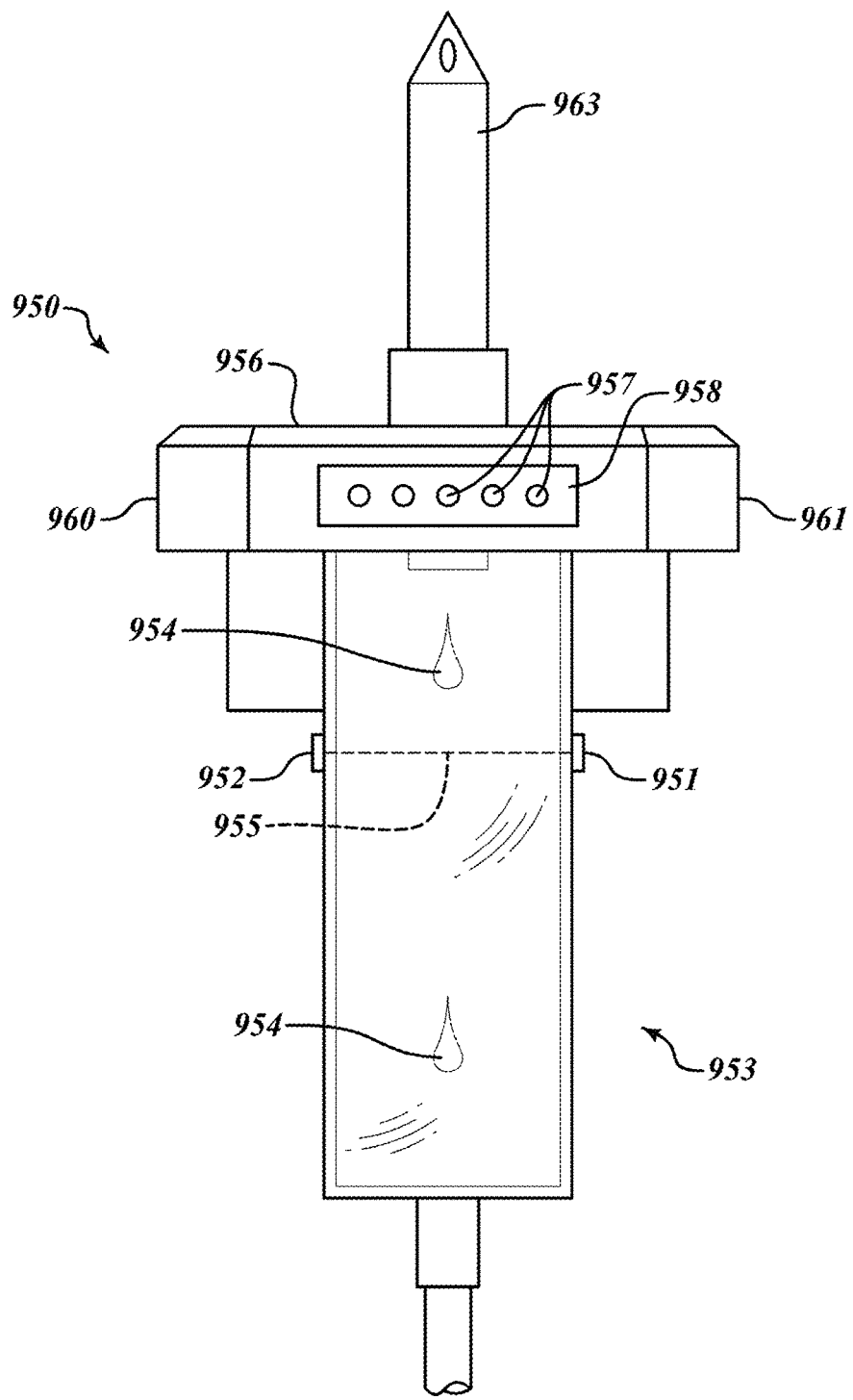
FIG. 10 is a front plan view of a drip chamber having an attached flow-rate sensor housing.
Figure 11:
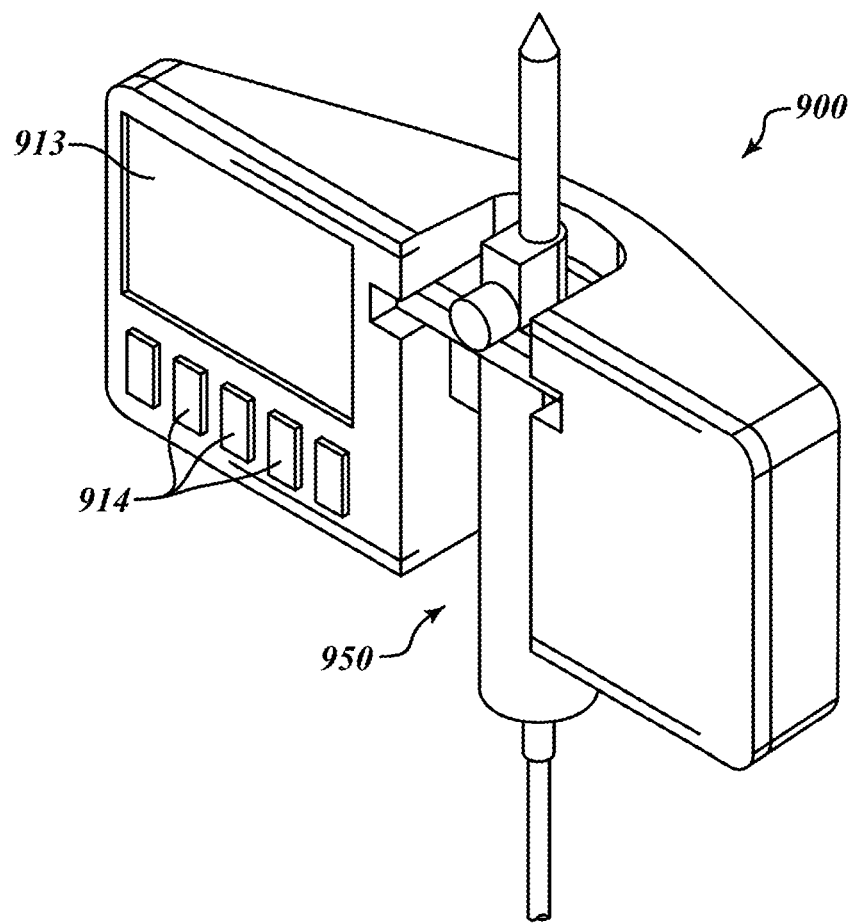
FIG. 11 is a perspective view of a preferred drip chamber and sensor housing attached to a monitoring device.

FIGS. 9-11 show an alternate version of a monitoring device 900 and a sensor device body 950, separated from one another in FIG. 9, interconnected in FIG. 11, and illustrating the sensor device body alone in FIG. 10. In one version of this alternate embodiment, the sensor device body 950 includes an infrared emitting diode 951, or IRED, and a photodiode 952, or PD (see FIG. 10), which are positioned about a tubing set 953 in such a way so that drops 954 falling from the top to the bottom of the tubing set will at least partially obscure or refract the beam 955 which extends along a line of sight from the PD to the IRED. Most preferably, the IRED and PD are attached to a housing 956 forming the sensor device body, and surrounding the tubing set or at least extending along diametrically opposite portions of the tubing set. In some versions, the sensor device body need not have a separate housing, but rather can comprise the tubing set itself, with the various components mounted to the tubing set. The sensor device body components (such as the IRED and PD) may be electrically connected to contacts 957 (best seen in FIG. 10) exposed on the exterior of the tubing set and preferably formed on a tab or projection 958 extending outwardly from the housing. The tubing set contacts 957 are configured to align with receiving contacts 910 mounted on the separate monitoring device 900 which attaches to the drip chamber and sensor device body. As discussed further below, the contacts 957 may facilitate the delivery of power to the housing, and enable data related to the PD or other aspects within the sensor device body to be exchanged with the monitoring device.

For simplicity of illustration, the embodiments of FIGS. 9-11 are illustrated without a fluid source. The tubing set and sensor device body are illustrated with an exemplary upper receiving tube 963 having an upper end in the form of a spike for insertion into a fluid source such as fluid source 191 as illustrated in FIG. 1.

In one version, the housing 956 includes a pair of lateral fins 960, 961 which are configured to be received within mating channels 911, 912 of the monitoring device, thereby ensuring a snug fit of the housing to the monitor, including the alignment of the sensor device body contacts 957 with the monitor contacts 910. Thus, most preferably the sensor device body includes structural features that allow it to mount to the monitoring device, and further in which the IRED and PD are mounted on the sensor device body rather than on the monitoring device. In such a version, the alignment of the components about the drip tube are not subject to movement or faulty attachment by a user because they are fixedly mounted in a proper location, diametrically opposite one another. The monitoring device 900 may otherwise be substantially similar to, or the same as, other versions of monitoring devices described above, having for example a display 913, a number of buttons 914 or other input/output interface devices, a trench 915 for receiving the tubing set, and an internal processor and memory for operating the monitoring device. The monitoring device may further be secured in place either with a mechanical latch, magnets, other mechanical features.

Most preferably, as noted above, in the embodiment as shown in FIGS. 9-11 at least the emitter and detector are fixedly mounted to the tubing set so that their alignment cannot be altered by a user. Thus, for example, the emitter, detector and power source may be glued or molded to the drip chamber, or mounted to the housing with the housing permanently glued or otherwise permanently attached to the tubing set so that the alignment is fixed in place. As used here, mounting using screws or bolts is within the meaning of "permanently attached" because they would require a tool for removal, and cannot be removed simply by a user squeezing the handles to urge apart a spring-loaded device, for example.

Figure 12:
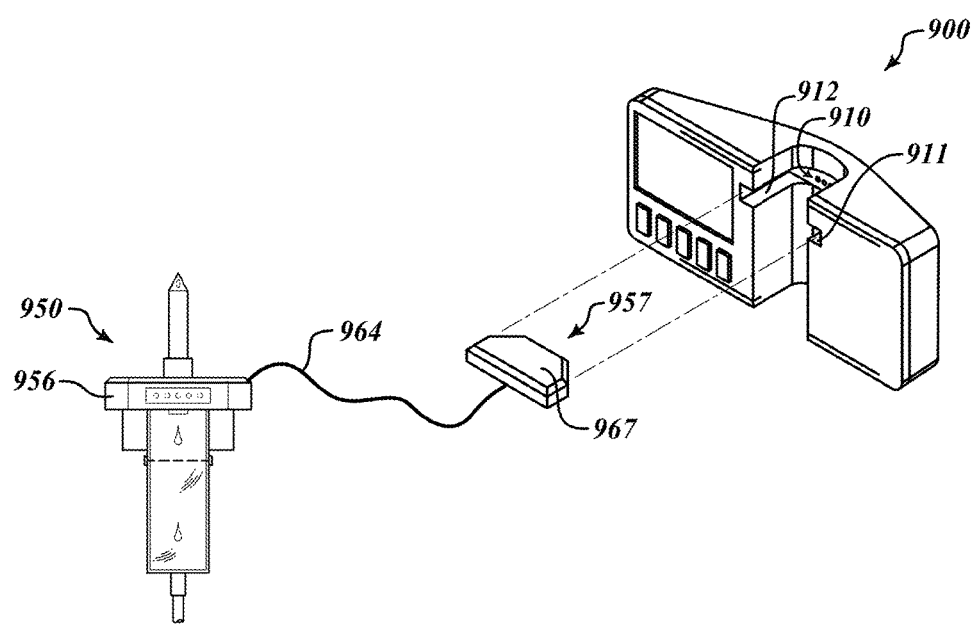
FIG. 12 is a schematic view of a preferred drip chamber and sensor housing having a wired tether and connector configured for attachment to a separate monitoring device.

In one embodiment, such as illustrated in FIG. 12, a wired tether is employed to link the tubing set to the monitoring device. One end of this tether may interface with the form factor and connector of the tubing set, and the other end may be connectable to a monitoring device, Thus, the tether may serve as an "extension cord," allowing the sensor and the monitoring device to be separated by some distance. Such a wired interface may employ a serial, e.g., RS232, connection, a USB connection, an Ethernet connection, an 12C connection, an SPI interface, or the like.

As one example, the sensor device body 950 includes a wire 964 extending from the sensor housing 956 and terminating in a coupler 967. The coupler is configured to mate with the monitoring device 900, and in one version the coupler is formed with an outer shape consistent with the sensor housing as described above, corresponding to the pair of lateral fins 960, 961. Consequently, the coupler is configured to be received within the mating channels 911, 912 of the monitoring device. The coupler further includes contacts such as those corresponding to the tubing set contacts 957 as described above, and which are configured to align with receiving contacts 910 mounted on the separate monitoring device 900. The tethered coupler therefor allows the monitoring device to be located at a distance from the tubing set and sensor housing, limited only by the length of the cord or cable 964.

Figure 13:
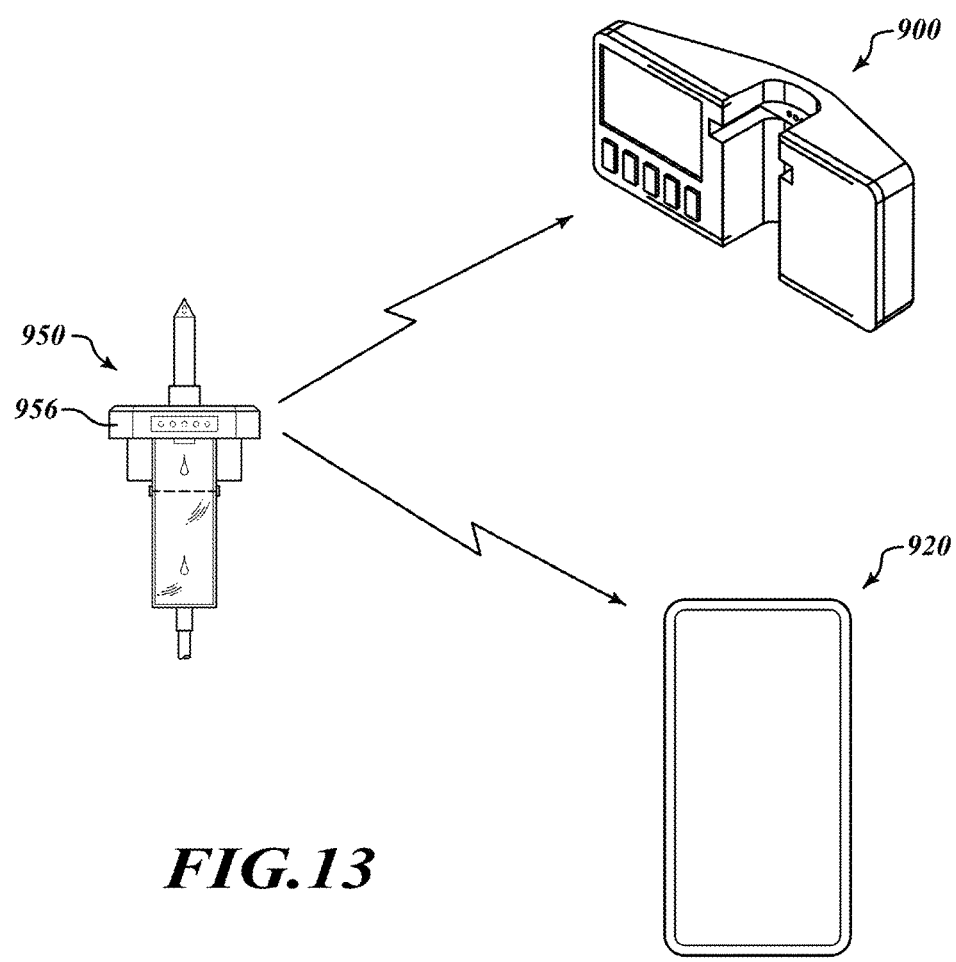
FIG. 13 is a schematic view of a preferred drip chamber and sensor housing in wireless communication with one or more separate monitoring devices.

In yet another one embodiment, as illustrated in FIG. 13, an embedded radio in the tubing set, or more preferably in the sensor device body 950 or its housing 956, can also be used to communicate with the monitoring device 900 wirelessly. In one version, the monitoring device as described above may include its own receiver, transmitter, or transceiver in order to send or receive signals to or from the sensor device body 950 wirelessly. Similarly, the sensor device body 950, preferably within the housing 956, includes a transceiver or equivalent components to enable such communication. In this configuration, the sensor device body may send data related to the monitoring of drips to the monitoring device, which can then store, analyze, and display the data accordingly at a remote location.

In one version, the monitoring device may be the same or substantially similar to the monitoring device as described above, other than the inclusion of components to enable wireless communication. In alternate versions the monitoring device may be configured differently, for example to exclude the trench, contacts, and other features for direct reception of the tubing set and sensor device body. In one such case, the monitoring device may be in the form of a personal computer or a tablet 920 containing stored programming instructions enabling the receipt and analysis of the data as described above. In other embodiments the monitoring device 920 may be a smartphone or other wireless-enabled device running software for interfacing wirelessly with the tubing set and sensor device body.

As illustrated in FIG. 13, the sensor device body 950 and monitoring device 900, 920 are indicated as communicating wirelessly with one another in a direct fashion, for example by using Bluetooth or other protocols. For example, a wireless link may include a USB link, a Bluetooth link, a Low Power Bluetooth link, a ZigBee link, a NFC link, and/or the like. It should be appreciated that the connection may be less direct, such as over a Wi-Fi or other wireless network, or even more remotely over the Internet or other networks.

Figure 14:
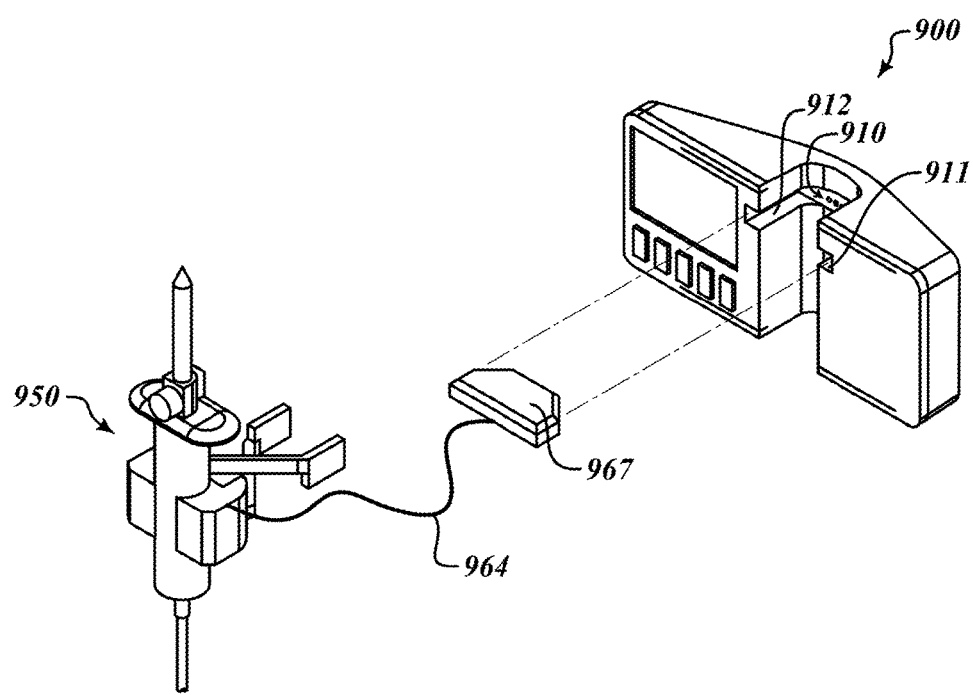
FIG. 14 is a schematic view of an alternate preferred drip chamber and sensor housing having a wired tether and connector configured for attachment to a separate monitoring device.
Figure 15:
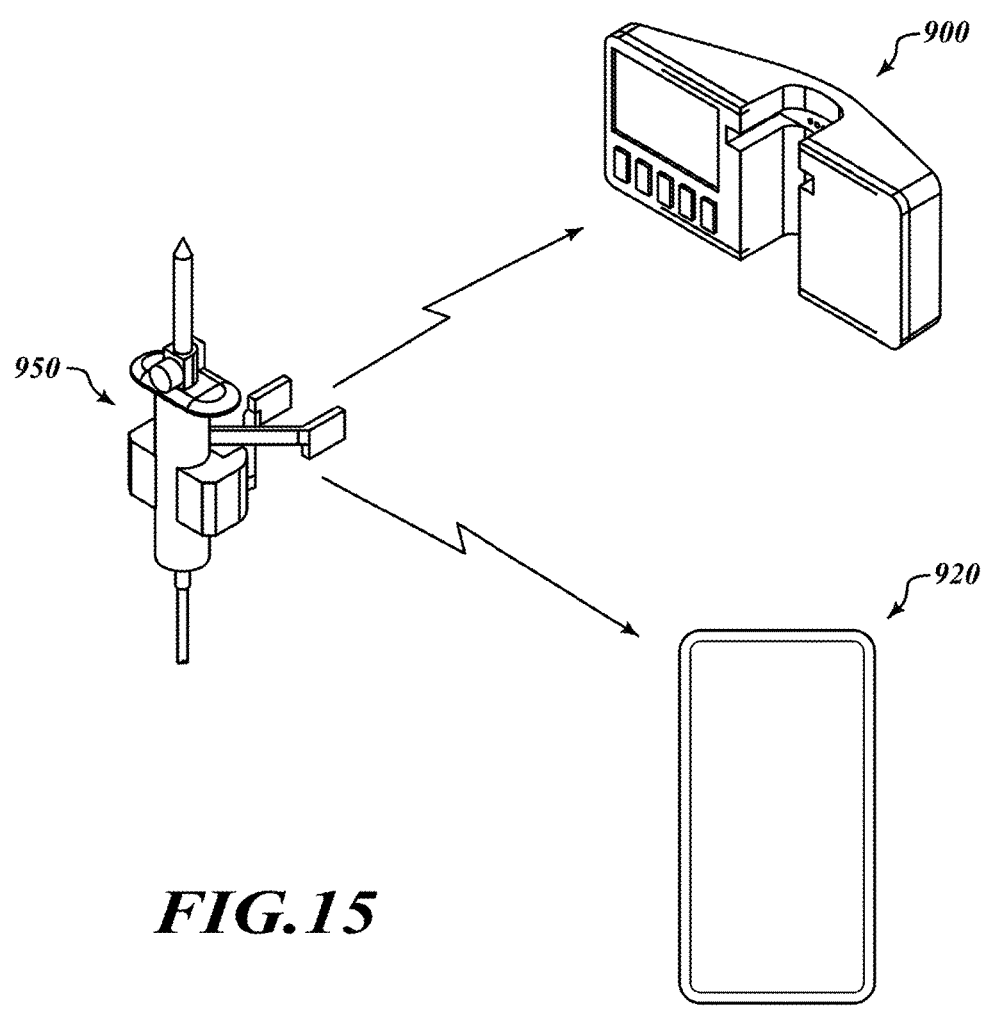
FIG. 15 is a schematic view of an alternate preferred drip chamber and sensor housing in wireless communication with one or more separate monitoring devices.

The devices in FIGS. 12 and 13 illustrate tethered and wireless connections between a sensor device body and a monitoring device, in which the sensor device body is permanently affixed to the tubing set. In other versions, the wireless or tethered connections may extend from a separate sensor device designed to clip or otherwise attach onto the exterior of standard tubing sets, such as the version as illustrated and described above with reference to FIGS. 2 and 3. This removable device may contain a drop sensor, and may be connected with a tether (see FIG. 14) or have components allowing it to wirelessly (see FIG. 15) communicate with a separate monitoring device. Such a removable device may be generally lighter than the above-discussed all-in-one devices, in which the monitoring device and display are incorporated into the sensor device body and attached to the tubing set directly. Also, such a device may enable more secure attachment and better sensor alignment when compared to an all-in-one device.

Certain embodiments of the present technology also include drop-sensing or other flow rate technologies other than infrared beam detection, including but not limited to RF, optical, and capacitive sensing technologies.

In certain embodiments, after receipt of the flow rate data by the monitoring device through wired or wireless means, the data may be further transmitted through a wired or wireless communications method to a remote monitoring station, which could be elsewhere in a facility or remotely located through a long-distance network. For example, as noted above, either of the monitoring devices 900, 920 may be located remotely and in communication with the sensor device body 950 over a wireless network which may include the Internet.

In additional embodiments, the same electromechanical or wireless interface is extended to sensors beyond drip rate measurement, such as pulse oximeters, respiratory or electrocardiac monitors, as well as interventional devices such as IV flow rate controllers, pumps, or SCDs (sequential compression devices). Thus, the sensor device body may be incorporated into a device other than a tubing set, in which the sensors monitor other parameters and convey the data in a fashion as described above.

In some versions, these electromechanical or wireless interfaces may contain a facility allowing such attachments (including the above-discussed tube sets) to "self-describe" to the monitoring device, which may then display appropriate control and status information depending on the nature of the attached sensor or interventional device.

Figure 16:
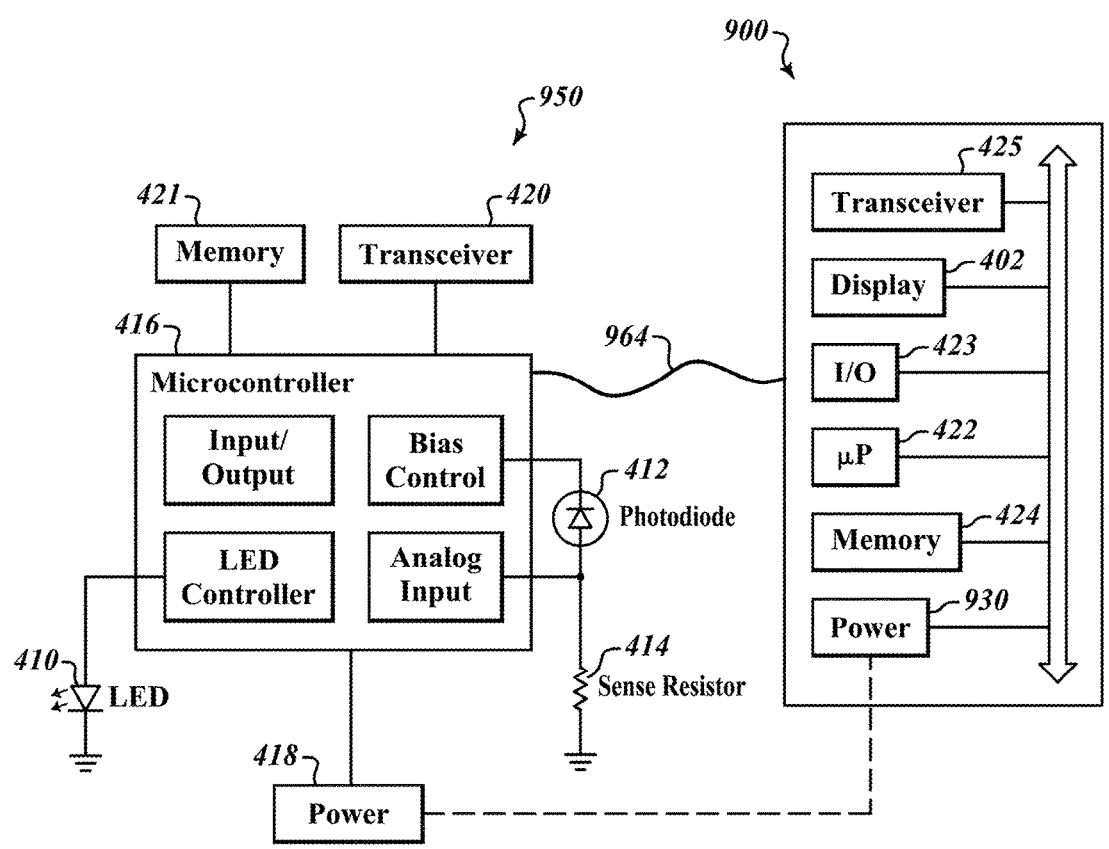
FIG. 16 is a block diagram of components in a preferred drip chamber sensor device body and separate monitoring unit.

FIG. 16. illustrates a block diagram of the internal components forming an electrical circuit of the preferred sensor device body 950 and monitoring device 900. The sensor device body includes a source, which may be in the form of an LED 410. At least one terminal of LED 410 may be tied to ground. A detector is also provided, which is preferably a photodiode 412. Photodiode 412 may have a greater sensitivity to IR wavelengths than to wavelengths within the visible light spectrum. A resistor 414 may be used in conjunction with the photodiode 414, connected between the photodiode 412 and ground.

In the illustrated example, a microcontroller 416 may control the operation of at least one of the LED 410 and photodiode 412. In some versions, however, a microcontroller may be omitted from the sensor device body 950. This may be desirable, for example, in versions in which the sensor device body connects directly (such as in FIG. 11) or through an optional tether 964 (such as in FIG. 12) to a monitoring device 900 having its own microcontroller or microprocessor. Within this description, the term "processor" will generally encompass processors, microprocessors, and microcontrollers. Where a processor is omitted from the sensor device body 950, the components of the sensor device body are preferably arranged for signal communication with, and control by, a processor within the monitoring device 900 via the contacts 910, 957, as described above.

The processor (whether in the sensor device body 950 or monitoring device 900) may control a pulsing of biasing currents used in the operation of LED 410 and photodiode 412, and may perform the other services as described above with reference to FIG. 4.

As illustrated, the sensor device body includes a source of power, 418, which may include a power supply in the form of an internal power supply, such as a battery or a cord for AC power. In some versions, however, the source of the power 418 may be provided from the separate monitoring device 900 and its internal power supply 930. The power in such a case is preferably delivered to the sensor device body via the contacts, as described above, and may be conveyed through the tether 964.

In the case of a wireless version of the sensor device body, a transceiver 420 is provided. The transceiver may alternatively be a transmitter, without a separate ability to receive signals from the monitoring device. Though not shown, the transceiver or transmitter includes an antenna.

Preferably, the sensor device body includes a memory 421, which may be used as a cache for data detected by the detector, for programming instructions operable by the microcontroller, or other purposes. The memory may also include identifying information such as a serial number or the like, which can be transmitted to or read by the monitoring device which can then interpret and display the identifying information to indicate which type of sensor device body is in use, and a particular such device which has been identified. The memory may further include stored information such as the tubing set's drip factor (gtt/mL), a sensor configuration, or yet other information which can be conveyed to a monitoring unit.

The monitoring device may include display unit 402, such as an LCD or LED screen. Display unit 402 may be employed to provide information to a user, including the information described above with reference to FIG. 4.

A processor 422 is provided within the monitoring device 900, along with a memory 424 containing stored programming instructions operable by the processor to cause the monitoring device to control the sensor device body, retrieve data from the sensor device body, read data from memory in the sensor device body, analyze and store data detected by the system, and control the display 402.

Monitoring devices may include a user input interface, or I/O device 423, which may be in the form of button inputs as described above, or which may alternatively be in the form of a touch screen or other interface. The monitoring devices may include an audio interface as part of the I/O subsystem, such as a speaker used to provide audio alerts and other audio information to a user.

A power supply 930 is provided, which may be in the form of batteries, an AC power supply, or others.

The monitoring device further includes a transceiver 425, which may be configured with an antenna to send and receive data to and from the sensor device body, or to and from a remote computer, either directly or indirectly through various communications channels as described above.

Figure 17:
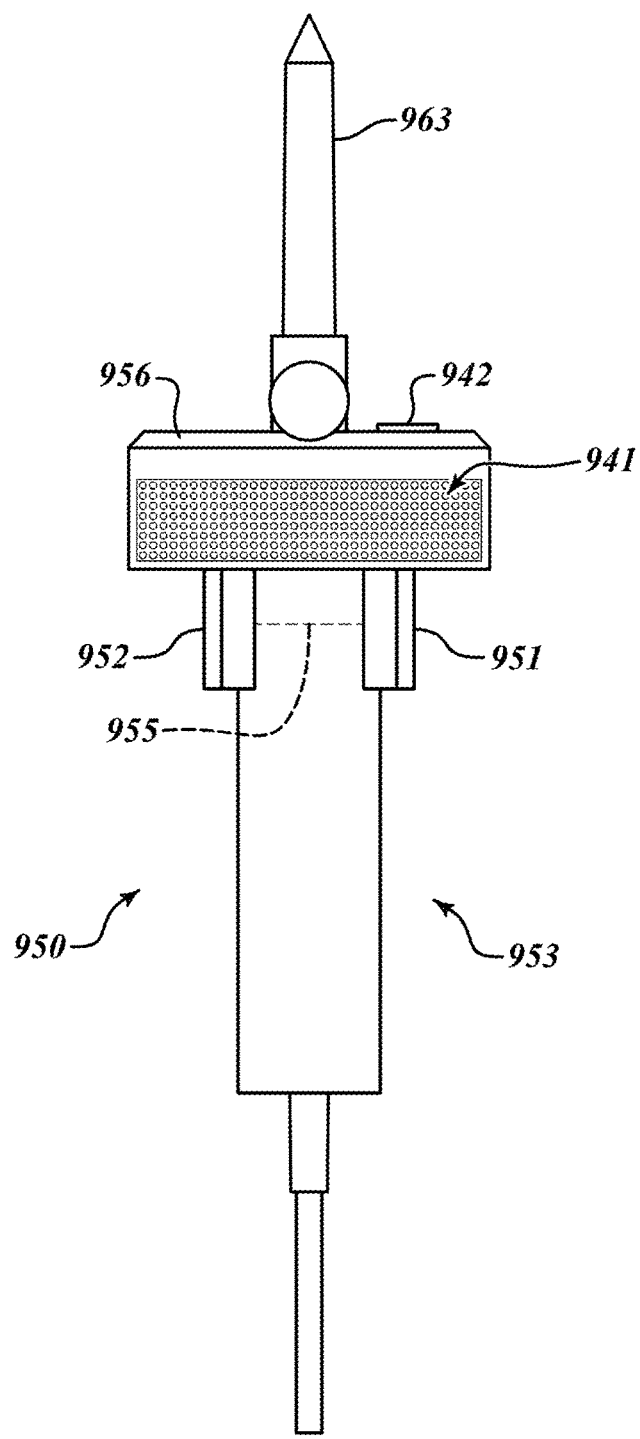
FIG. 17 is a schematic view of an alternate preferred drip chamber and sensor housing.

A further alternate embodiment of a device for monitoring fluid through a drip chamber is illustrated in FIG. 17. In this version, the device includes a tubing set and sensor device body, illustrated with an exemplary upper receiving tube 963 having an upper end in the form of a spike for insertion into a fluid source such as fluid source 191 as illustrated in FIG. 1. In alternate embodiment, the sensor device body 950 preferably includes an infrared emitting diode 951, or IRED, and a photodiode 952, or PD (see FIG. 10), which are positioned about a tubing set 953 in such a way so that drops falling from the top to the bottom of the tubing set will at least partially obscure or refract the beam 955 which extends along a line of sight from the PD to the IRED. As noted above, the IRED and PD may alternately be any other form of sensor configured to detect drips falling through the sensor device body.

Most preferably, the IRED and PD are attached to a housing 956 forming the sensor device body, and surrounding the tubing set or at least extending along diametrically opposite portions of the tubing set. In some versions of this alternate embodiment, the sensor device body need not have a separate housing, but rather can comprise the tubing set itself, with the various components mounted to the tubing set. Most preferably, the components are permanently affixed to the drip set, such as by gluing, molding, sonic welding, or using other such methods.

The alternate embodiment of FIG. 17, in some implementations, is capable of serving as a stand-alone device, without a separate or remote monitoring unit or display. Accordingly, the sensor device body includes (either in the housing 956, or otherwise attached to the tubing set) a microcontroller 416 to control the operation of at least the LED and PD, as well as the related components discussed with reference to FIG. 16. The processor controls the operation of LED and PD, and may perform the other services as described above.

The sensor device body also includes a source of power 418 (see FIG. 16), which is not illustrated in FIG. 17 but which may be provided within the housing 956 or otherwise attached to the device. The power supply may be in the form of an internal power supply, such as a battery, or may be a cord for AC power, a solar array strip, or have yet other forms.

Most preferably, this alternate version of the invention includes a display panel 941, which may be in the form of an LED or LCD display, for example, capable of displaying text messages, icons, or other images. In other versions, the display panel may be more simple, such as one or more LEDs or other indicators which may convey messages through blinking, illumination, display of a particular color, or other formats. In the illustrated example, the display panel is provided on an exterior surface of the housing 956. The display panel is controlled by the microcontroller, such as described above.

The version of FIG. 17 also preferably includes a user input device, which in the illustrated example is in the form of a button 942 provided on the housing 956 and in communication with the microcontroller 416. The button enables a user to toggle the device on or off, and to scroll through and select various possible commands to control the device. Some versions may include multiple buttons or switches attached to the device, or may incorporate a touch screen into the display panel 941 to serve as both a display and user input device.

The version of FIG. 17 is suitable, in some implementations, to serve as a disposable unit, with all of the necessary components built into and attached to the device. Such a version may optionally include a transceiver 420 (see FIG. 16) to enable it to communicate with a remote monitoring unit. The device may further optionally include contacts or a tether for direct connection with a monitoring unit, allowing a user to selectively use the device in a stand-alone manner, through physical attachment to a monitoring device, or though wireless communication with a remote monitoring device.

Preferably, the sensor device body includes a memory 421 as described above, which may be used as a cache for data detected by the detector, for programming instructions operable by the microcontroller, or other purposes such as described above.

FIGS. 18-19 show additional views of a preferred monitoring device 800 and a tubing set 953. The tubing set of FIGS. 18-19 does not include an integrated sensor device body (such as sensor device body 950, described above). Instead, the tubing set is in the form of a separate drip chamber such as in FIGS. 1A and 3, to be used in a manner in which it may be attached or mounted to a separate monitoring device such as that of FIGS. 8A-C. The tubing set as illustrated in FIG. 18 includes a collar 975 shown in a partially exploded view. The tubing set (and collar) are shown separated from the monitoring device in FIG. 18, with the monitoring device also being shown alone in FIG. 19.

As with the monitoring device of FIGS. 8A-C, the monitoring device in FIGS. 18-19 includes an emitter or source 810 such as an infrared emitting diode, or IRED. An opposing detector 811 is visible in FIG. 19, positioned in opposition along the inner surface of the trench 864 as described above with reference to FIGS. 8A-C. When the tubing set is mounted in the trench, the source and detector are positioned about the tubing set 953 in such a way so that drops falling from the top to the bottom of the tubing set will at least partially obscure or refract the beam which extends along a line of sight from the source or emitter to the detector.

The monitoring device 800 may include display unit 802, user input interface 806, and user audio interface 808, in the same manner as described above.

The tubing set is illustrated with an exemplary upper receiving tube 963 having an upper end in the form of a spike for insertion into a fluid source such as fluid source 191 as illustrated in FIG. 1.

In one version, the collar 975 includes an upper opening 977 to allow the spike 963 and an upper portion of the tubing set to pass through the opening as the collar surrounds the upper portion of the tubing set. The collar also includes a peripheral radially-extending flange 976, in the manner of the fins 960, 961 described above. Preferably, the flange 976 is in the form of an annular flange which surrounds the collar and encircles the tubing set when attached to the tubing set. The collar may be permanently attached to the tubing set, or in other versions may be removably attachable.

The monitoring device includes a tubing set mount in the form of an attachment location preferably configured as a pair of mating channels such as channels 911, 912 described above and illustrated in FIG. 14. The flange is configured to be received within the mating channels of the monitoring device, thereby ensuring a snug fit of the housing to the monitor, including the alignment of the tubing set with respect to the emitter and detector. Thus, most preferably the tubing set (or collar) includes structural features that allow it to mount to the monitoring device, and further in which the IRED and PD are mounted on the monitoring device so that have a line of sight through the drip tube and are not subject to movement or faulty attachment by a user because they are fixedly mounted in a proper location, diametrically opposite one another. As described above, the tubing set may further be secured in place either with a mechanical latch, magnets, other mechanical features.

In the version particularly illustrated in FIGS. 18 and 19, the channels 823, 825 of the monitoring device 800 are positioned at the top of the device, formed in an opposing pair of brackets 822, 824 which extend toward one another, and in a direction toward the trench 864 in each case. The flange 976 is configured to be snugly received within the channels 823, 825 in order to firmly hold the collar 975 and tubing set 953 in place within the trench 864. Most preferably, the interior shape of the channels within the brackets is in the form of a mating arc corresponding to the shape of the annular flange, such that the annular flange will be snugly and frictionally held within the channels, and further in which the annular flange can rotate while being held within the channels while holding the tubing set and drip tube in the same position with respect to its central axis.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A monitoring device for monitoring fluid passing through a drip tube of a tubing set, comprising:
   an emitter mounted on the monitoring device;
   a detector mounted on the monitoring device;
   the emitter being positioned to emit electromagnetic radiation toward the detector;
   the detector being positioned relative to the emitter receive to receive the electromagnetic radiation from the emitter and to generate a detector signal in response to electromagnetic radiation received from the emitter;
   a tubing set mount positioned on the monitoring device, the tubing set mount being configured to receive a portion of the tubing set such that when the portion of the tubing set is received within the tubing set mount the tubing set is mechanically aligned in a fixed position, wherein the electromagnetic radiation passes centrally through the drip tube from the emitter to the detector.

2. The monitoring device of claim 1, wherein the tubing set mount comprises at least one channel and wherein the tubing set comprises a flange, the at least one channel being configured to receive and retain the flange.

3. The monitoring device of claim 2, wherein the tubing set is removably attachable to the tubing set mount by insertion of the flange into the at least one channel.

4. The monitoring device of claim 3, wherein the at least one channel comprises a first channel and an opposing second channel.

5. The monitoring device of claim 4, further comprising a first bracket and an opposing second bracket, the first channel being formed in the first bracket and the second channel being formed in the second bracket.

6. The monitoring device of claim 5, further comprising a trench defined in the monitoring device between the first channel and the second channel, wherein the tubing set is positioned in the trench when the tubing set is received within the tubing set mount.

7. The monitoring device of claim 3, wherein the at least one channel is positioned at the top of the monitoring device.

8. The monitoring device of claim 3, wherein the flange comprises an annular flange.

9. A monitoring device for monitoring fluid passing through a drip tube of a tubing set, comprising:
   an emitter mounted on the monitoring device;
   a detector mounted on the monitoring device;
   the emitter being positioned to emit electromagnetic radiation toward the detector;
   the detector being positioned relative to the emitter receive to receive the electromagnetic radiation from the emitter and to generate a detector signal in response to electromagnetic radiation received from the emitter;
   a processor in communication with the detector;
   a memory having stored programming instructions operable by the processor to detect a fluid drop passing through the drip tube based on the detector signal; and
   a tubing set mount positioned on the monitoring device, the tubing set mount being configured to receive a collar attached to the tubing set such that when the collar is received within the tubing set mount the tubing set is mechanically aligned in a fixed position and the electromagnetic radiation passes centrally through the drip tube from the emitter to the detector.

10. The monitoring device of claim 9, wherein the tubing set mount comprises a first channel and a second channel, the first channel being positioned opposite the second channel whereby the collar is receivable within each of the first channel and the second channel to removably retain the tubing set to the monitoring device.

11. The monitoring device of claim 10, further comprising a first bracket and an opposing second bracket, the first channel being formed in the first bracket and the second channel being formed in the second bracket.

12. The monitoring device of claim 10, further comprising a trench defined in the monitoring device between the first channel and the second channel, wherein the tubing set is positioned in the trench when the tubing set is received within the tubing set mount.

13. The monitoring device of claim 10, wherein the tubing set mount is positioned at the top of the monitoring device.

14. The monitoring device of claim 10, wherein the collar comprises an annular flange.

15. The monitoring device of claim 14, wherein the annular flange is receivable within the tubing set mount, whereby the tubing set is rotatable within the tubing set mount while maintaining the tubing set in the mechanically aligned position.

* * * * *